Figure 6A:
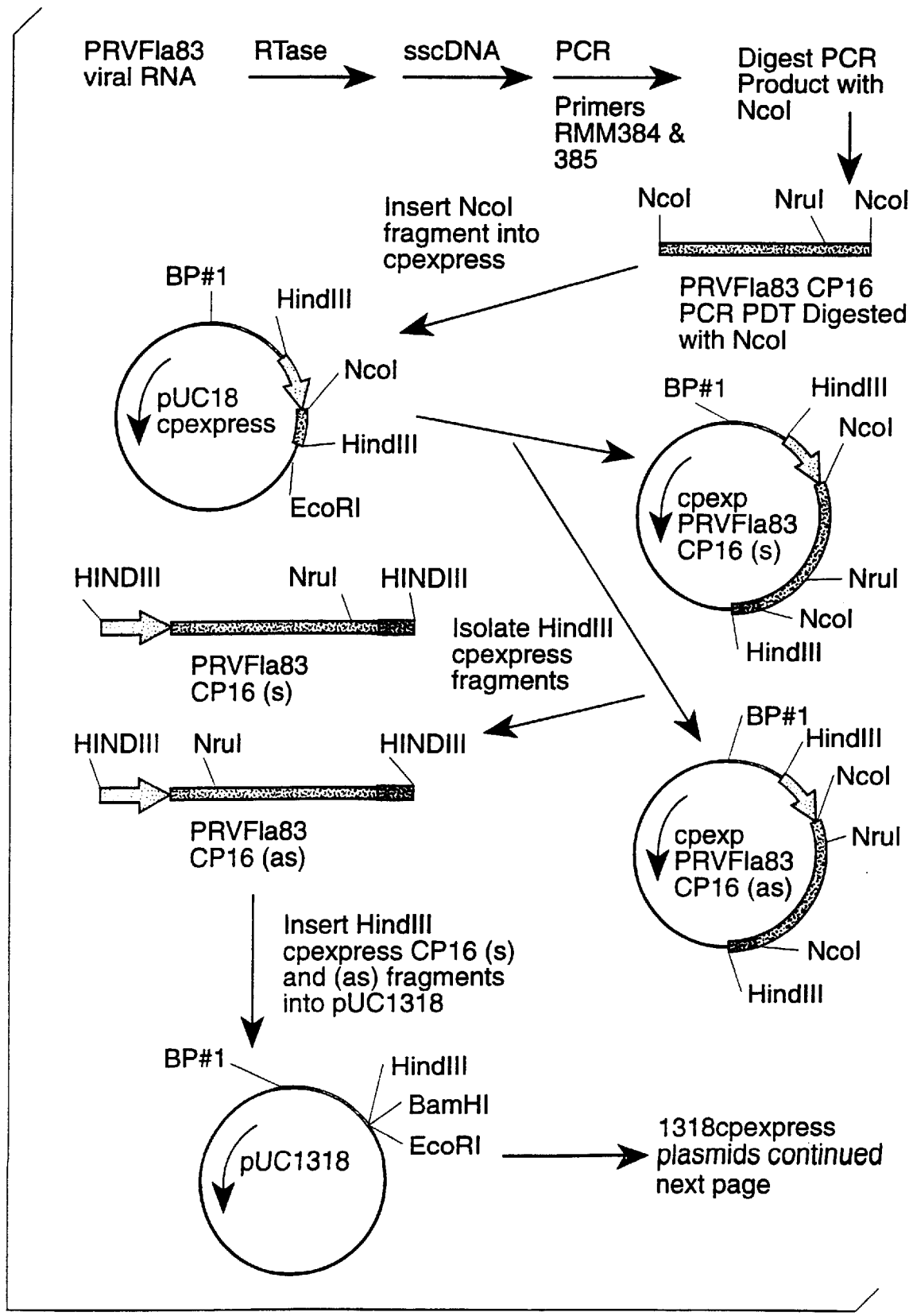

United States Patent [19]
McMaster et al.

[11] Patent Number: 6,002,072
[45] Date of Patent: Dec. 14, 1999

[54] COAT PROTEIN GENE FOR THE FLA83 W STRAIN OF PAPAYA RINGSPOT VIRUS

[75] Inventors: Russell J. McMaster, Kenosha, Wis.; Maury L. Boeshore, Wauconda, Ill.; David M. Tricoli, Davis, Calif.; John F. Reynolds, Davis, Calif.; Kim J. Carney, Davis, Calif.; Dennis Gonsalves, Geneva, N.Y.

[73] Assignees: Seminis Vegetable Seeds, Inc., Saticoy, Calif.; Cornell Research Foundation, Inc., Ithaca, N.Y.

[21] Appl. No.: 08/860,368

[22] PCT Filed: Jun. 7, 1995

[86] PCT No.: PCT/US95/07272

§ 371 Date: Nov. 3, 1997

§ 102(e) Date: Nov. 3, 1997

[87] PCT Pub. No.: WO96/21019

PCT Pub. Date: Jul. 11, 1996

Related U.S. Application Data

[63] Continuation-in-part of application No. 08/366,881, Dec. 30, 1994, abandoned.

[51] Int. Cl.[6] .............................. A01H 5/00; C12N 1/21; C12N 5/14; C12N 15/40; C12N 15/82
[52] U.S. Cl. .................. 800/301; 435/252.2; 435/252.3; 435/320.1; 435/419; 536/23.72; 800/280
[58] Field of Search ...................... 536/23.72; 435/320.1, 435/252.3, 419, 468, 252.2; 800/279, 280, 301

[56] References Cited

U.S. PATENT DOCUMENTS 5,162,601  11/1992  Slightom ................................. 800/205

FOREIGN PATENT DOCUMENTS

WO 90/02184  3/1990  WIPO ............................. C12N 15/40

OTHER PUBLICATIONS

Bateson et al., *Arch–Viol*, 123, 101 (1992).
Beven et al., *Nucleic Acids Res.*, 11, 369 (1983).
Carrington et al., *J. Virol.*, 61, 2540 (1987).
Clark, et al., *J. Gen. Virol.*, 34, 475 (1979).
Crossway et al., *Mol. Gen. Genet.*, 202, 179 (1985).
Depicker et al., *J.Mol Appl. Genet.*, 1, 561 (1982).
Dougherty et al., *Ann. Rev. Phytopath.*, 26, 123 (1988).
Fitch et al., *Bio/Technology*, 10, 1466 (1992).
Fitchen et al., *Annu Rev. Microbiol.*, 47, 739 (1993).
Fromm et al., *Proc. Natl. Acad. Sci. USA*, 82, 5824 (1985).
Gonsalves, *American J. Bot.*, 79, 88 (1992).
Kay et al., *Nuc. Acids Res.*, 15, 2778 (1987).
Klein et al., *Nature*, 327, 70 (1987).
Ling, et al., *Bio/Technology*, 9, 752 (1991).
Luis et al., *Hortscience*, 29, 483 (1994).
Namba et al., *Gene*, 107, 181 (1991).
Namba et al., *Phytopathology*, 82, 940 (1992).
Paszowski et al., *EMBO J.*, 3, 2717 (1984).
Quemada et al., *J. Gen Virol.*, 71, 1065 (1989).
Quemada et al., *J. Gen Virol.*, 71, 203 (1990).
Restrepo–Hartwig et al., *J. Virol.*, 66, 5662 (1992).
Smith et al., *Nature*, 334: 724 (1988).
Tennant et al., *Phytopathology*, 84, 1359 (1994).
Van der Krol et al., *Nature*, 333: 866 (1988).
Wang et al., *Phytopathology*, 84, 1205 (1994).
Wilson, *Proc. Natl. Acad. Sci. USA*, 90, 3134 (1993).
Wu, ed., *Methods in Enzymology*, 68 (1979).
Yeh et al., *J.Gen Virol.*, 73:2531 (1992).
Yeh et al., *Phytopath.*, 74, 1081 (1984).

*Primary Examiner*—Lynette R. F. Smith
*Assistant Examiner*—Amy J. Nelson
*Attorney, Agent, or Firm*—Rockey, Milnamow & Katz, Ltd.

[57] ABSTRACT

The present invention relates to a coat protein gene of papaya ringspot virus strain FLA83 W. This coat protein gene can be used to prepare plants which are resistant to papaya ringspot virus.

15 Claims, 22 Drawing Sheets

FIG. 1A

```
  1 ATGGCTCCATTCAATGAGCTGGCGAAACAAGGGAGGGCCCATACGTCTCCGAAGTTGGATTAAGAAGTTGTATACGTGTGAACGCGGATCAGTGGATG   100
    MetAlaProPheAsnGluLeuAlaLeuAlaLysGlnGlyArgAlaProTyrValSerGluValValGlyLeuArgArgLeuTyrThrCysGluArgGlySerValAspG
    M   A   P   F   N   E   L   A   K   Q   G   R   A   P   Y   V   S   E   V   V   G   L   R   R   L   Y   T   C   E   R   G   S   V   D   E

101 AATTGGAAGCGTATATAGATAAATATTTTGAGCGTGAGAGGGGAGACTCACCCGAAGTACTGGTGTACCATGAATCAAGGAGTACTGATGATTATGAACT   200
    luLeuGluAlaTyrIleAspLysTyrPheGluArgGluArgGlyAspSerProGluValLeuValTyrHisGluSerArgSerThrAspAspTyrGluLe
    L   E   A   Y   I   D   K   Y   F   E   R   E   R   G   D   S   P   E   V   L   V   Y   H   E   S   R   S   T   D   D   Y   E   L

201 TGTTCGTGTCAACAATACACATGTGTTCATCAAGCCAAAAATGAAGCTGTGGACGCTGGTTGAACGAAAAGCTCAAGAAAAAGAAAAACAGAGAGAG   300
    uValArgValAsnAsnThrHisValPheHisGlnAlaLysAsnGluAlaValAspAlaGlyLeuAsnGluLysLeuGluLysGlnArgGlu
    V   R   V   N   N   T   H   V   F   H   Q   A   K   N   E   A   V   D   A   G   L   N   E   K   L   K   E   K   Q   R   E

301 AAAGAAAAAGAAAAACAAAAAGAGAAAAAGATGATGCTAGTGACGAAAATGATGTGTAACTAGCACAAAACTGGAGCAGAGAGATAGAGATGTCA   400
    LysGluLysLysGluLysLysGlnLysGluLysLysAspAspAlaSerAspGlyAsnAspValLeuThrSerThrLysThrGlyGluArgAspArgAspValA
    K   E   K   Q   K   E   K   D   D   A   S   D   G   N   D   V   L   T   S   T   K   T   G   E   R   D   R   D   V   N

401 ATGTTGGAACTAGTGGGACTTTCACTATTCCAAGGATTAAACCATTCAATGATAAGATGATTTTACCGAGAATTAAGGAAAAACTGTCCTTAATTAAA   500
    snValGlyThrSerGlyThrPheThrIleProThrIleProArgIleLeuProArgIleLeuLysThrValLeuAsn
    V   G   T   S   G   T   F   T   I   P   R   I   K   P   F   N   D   K   M   I   L   P   R   I   K   G   K   T   V   L   N   L   N

501 TCATCTTCTTCAGTATAATCCGCAACAAATTGACATTTCGAACACTCTGCCACTCAGTCACAATTGAAAAATGCCACGAGGAGTGAGGAATGATTAT   600
    nHisLeuLeuGlnTyrAsnProGlnIleAspIleSerAsnThrArgAlaThrGlnSerGlnPheGluLysTrpHisGluGlyValArgAsnAspTyr
    H   L   Q   Y   N   P   Q   Q   I   D   I   S   N   T   R   A   T   Q   S   Q   F   E   K   W   H   E   G   V   R   N   D   Y

601 GGCCTGAATGATAAAGAGATGGAAGTAATGTTAAAATGGCTTGATGGTTGGTGTATTGAGAATGGTACATCTCCGGACATATCTGGTCTCGGTTATGA   700
    GlyLeuAsnAspLysGluMetGluValMetLeuAsnGlyLeuMetValTrpCysIleGluAsnGlyThrSerProAspIleSerGlyValTrpValMetM
    G   L   N   D   K   E   M   E   V   M   L   N   G   L   M   V   W   C   I   E   N   G   T   S   P   D   I   S   G   V   W   V   M   M
```

FIG. 1B

```
701  TGGATGATACTACAGGAACCCAAGTTGATTATCCAATCAAGCCTTTAATTGAGCATGCTACTCCGTCATTTAGGCAAATTATGGCTCACTTTAGTAACGC
     etAspAspThrThrGlyThrGlnValAspTyrProIleLysProLeuIleGluHisAlaThrProSerPheArgGlnIleMetAlaHisPheSerAsnAl
      D  D  T  T  G  T  Q  V  D  Y  P  I  K  P  L  I  E  H  A  T  P  S  F  R  Q  I  M  A  H  F  S  N  A

801  GGCAGAAGCATACATTGCAAGGAGAGAAATGCTACTGAGAGGTACATGCCGGGTATGGAATCAAGAGAAATTTGACTGACATTAGCCTCGCTAGATACGCT
     aAlaGluAlaTyrIleAlaArgArgAsnAlaThrGluArgTyrMetProArgTyrGlyIleLysArgAsnLeuThrAspIleSerLeuAlaArgTyrAla
      A  E  A  Y  I  A  R  R  N  A  T  E  R  Y  M  P  R  Y  G  I  K  R  N  L  T  D  I  S  L  A  R  Y  A

901  TTCGATTTCTATGAGGTTAATTCGAAAACACCTGATAGGGCTCGCGAAGCTCCATGCAGATGAAAGCTCGCGAAACACTAATCGCAGAATGT
     PheAspPheTyrGluValAsnSerLysThrProAspArgAlaArgGluAlaArgMetGlnMetLysAlaAlaAlaLeuArgAsnThrAsnArgArgMetP
      F  D  F  Y  E  V  N  S  K  T  P  D  R  A  R  E  A  R  M  Q  M  K  A  A  A  L  R  N  T  N  R  R  M  F

1001 TTGGTATGGACGGCAGTGTCAGTAACAAGGAAGAAAATACGGAGAGACACACAGTGGAAGATGTCAATAGAGACATGCACTCTCCTGGTATGCGCAA
     heGlyMetAspGlySerValSerAsnLysGluGluAsnThrGluArgHisThrValGluAspValAsnArgAspMetHisSerLeuLeuGlyMetArgAs
      G  M  D  G  S  V  S  N  K  E  E  N  T  E  R  H  T  V  E  D  V  N  R  D  M  H  S  L  L  G  M  R  N

1101 CTGAATACTCGCGCTTGTGTTTGTCGAGTCTAACTCGACCCTGTTTCACCCCATGG   1158
     nEndIleLeuAlaLeuValCysLeuSerSerLeuThrArgProCysPheThrProTrp
      *  I  L  A  L  V  C  L  S  S  L  T  R  P  C  F  T  P  W
```

800
900
1000
1100

FIG. 2A

```
  1 CCATGGCCAAGAATGAAGCTGTGGACGCTGGTTTGAACGAAAAGCTCAAAGAAAAGCAAAGAAAAAACAGAGAAAGAAAAAAGAGAAAGA     100
    MetAlaLysAsnGluAlaValAspAlaGlyLeuAsnGluLysLeuLysGluLysGlnLysGluLysLysGluLysGlnLysGluLysGl
    M  A  K  N  E  A  V  D  A  G  L  N  E  K  L  K  E  K  Q  K  E  K  K  E  K  Q  K  E  K  E

101 AAAAGATGATGCTAGTGACGGAAATGATGTTTAACTAGCACAAAACTGGAGAGAGATAGAGATGTCAATGTTGGAACTAGTGGACTTTCACTATT     200
    uLysAspAspAlaSerAspGlyAsnAspValLeuThrSerThrLysThrGlyGluArgAspArgAspValAsnValGlyThrSerGlyThrPheThrIle
    K  D  D  A  S  D  G  N  D  V  L  T  S  T  K  T  G  E  R  D  R  D  V  N  V  G  T  S  G  T  F  T  I

201 CCAAGGATTAAACCATTCAATGATAAGATGATTTTACCGAGAATTAAGGGAAAAACTGTCCTTAATTTAAATCATCTTCTTCAGTATAATCCGCAACAAA     300
    ProArgIleLysProPheAsnAspLysMetIleLeuProArgIleLysGlyLysThrValLeuAsnLeuAsnHisLeuLeuGlnTyrAsnProGlnGlnI
    P  R  I  K  P  F  N  D  K  M  I  L  P  R  I  K  G  K  T  V  L  N  L  N  H  L  L  Q  Y  N  P  Q  Q  I

301 TTGACATTTCGAACACTCGTGCCACTCAGTCACAATTTGAAAAATGGCACGAGGGAGTGAGGAATGATTATGCCTGAATGATAAAGAGATGGAAGTAAT     400
    leAspIleSerAsnThrArgAlaThrGlnSerGlnPheGluLysTrpHisGluGlyValAlaArgAsnAspTyrGlyLeuAsnAspLysGluMetGluValMe
    D  I  S  N  T  R  A  T  Q  S  Q  F  E  K  W  H  E  G  V  R  N  D  Y  G  L  N  D  K  E  M  E  V  M

401 GTTAAATGGCTTGATGGTTTGGTGTTGTATTGAGAATGTACATCTCCGGACATATCTGGTCTCTCGGTTATGATGGATGATACTACAGGAACCCAAGTTGAT     500
    tLeuAsnGlyLeuMetValTrpCysIleGluAsnGlyThrSerProAspIleSerGlyValTrpValMetMetAspAspThrThrGlyThrGlnValAsp
    L  N  G  L  M  V  W  C  I  E  N  G  T  S  P  D  I  S  G  V  W  V  M  M  D  D  T  T  G  T  Q  V  D

501 TATCCAATCAAGCCTTTAATTGAGCATGCTACTCCGTCATTTAGGCAAATTATGGCTCACTTTAGTAACGGCAGAAGCATACATTGCAAGGAGAAATG     600
    TyrProIleLysProLeuIleGluHisAlaThrProSerPheArgGlnIleMetAlaHisPheSerAsnAlaAlaGluAlaTyrIleAlaArgArgAsnA
    Y  P  I  K  P  L  I  E  H  A  T  P  S  F  R  Q  I  M  A  H  F  S  N  A  A  E  A  Y  I  A  R  R  N  A
```

FIG. 2B

```
601  CTACTGAGAGGTACACATGCCGCCGGTATGGAATCAAGAGAAATTTGACTGACATTAGCCTCGCTAGATACGCTTTCGATTTCTATGAGGTAATTCGAAAAC
     laThrGluArgTyrMetProArgTyrGlyIleLysArgAsnLeuThrAspIleSerLeuAlaArgTyrAlaPheAspPheTyrAlaValAsnSerLysTh
      T  E  R  Y  M  P  R  Y  G  I  K  R  N  L  T  D  I  S  L  A  R  Y  A  F  D  F  Y  E  V  N  S  K  T

701  ACCTGATAGGGCTCGGCAAGCTCACATGCAGATGAAAGCTGCAGAATGTTTGGTATGGACGGCAGTGTCAGTAACAAG
     rProAspArgAlaArgGluAlaHisMetGlnMetLysAlaAlaAlaAlaLeuArgAsnThrAsnArgArgMetPheGlyMetAspGlySerValSerAsnLys
      P  D  R  A  R  E  A  H  M  Q  M  K  A  A  A  L  R  N  T  N  R  R  M  F  G  M  D  G  S  V  S  N  K

801  GAAGAAATACGGAGAGACACAGTGGAAGATGTCAATAGAGACATGCACTCTCCTGGGTATGCCAACTGAATACTCGGCTTGTGTGTTTGTGTGTCA
     GluGluAsnThrGluArgHisThrValGluAspValAsnArgAspMetHisSerLeuLeuGlyMetArgAsnEndIleLeuAlaLeuValCysLeuSerS
      E  E  N  T  E  R  H  T  V  E  D  V  N  R  D  M  H  S  L  L  G  M  R  N  *  I  L  A  L  V  C  L  S  S

901  GTCTAACTCGACCCTGTTTCACCCCATGG  929
     erLeuThrArgProCysPheThrProTrp
      L  T  R  P  C  F  T  P  W
```

FIG. 3A

```
                                                   RMM384--->5'CGCAGATTTTACGAATTCGTTCTTG
     NcoI
     CCATGGCTCCATTCAATGAG
LG  1 CCATGGCTCCATTCAATGAGCTGGCGAAACAAGGGAGGGCCCCATACGTCTCGGAAGTTGGATTAAGAAGTTGTATACGTGTGAACGCGATCAGTGGA    100
     MetAlaProPheAsnGluLeuAlaLysGlnGlyArgAlaProTyrValSerGluValGlyLeuArgArgLeuTyrThrCysGluArgGlySerValAs
     M   A   P   F   N   E   L   A   K   Q   G   R   A   P   Y   V   S   E   V   G   L   R   R   L   Y   T   C   E   R   G   S   V   D

LG 101 TGAATTGGAAGCGTATATAGATAAATATTTTGAGCGTGAGAGGGGAGACTCACCCGAAGTACTGGTGTACCATGAATCAAGGAGTACTGATGATTATGAA    200
     pGluLeuGluAlaTyrIleAspLysTyrPheGluArgGluArgGlyAspSerProGluLeuValTyrHisGluSerArgSerThrAspAspTyrGlu
     E   L   E   A   Y   I   D   K   Y   F   E   R   E   R   G   D   S   P   E   V   L   V   Y   H   E   S   R   S   T   D   D   Y   E

RMM388--->5' AACAATACGCATGTGTTCCCATGGCCCAAGAATGAAGCTCTGGAC
                                         NcoI
LG 201 CTTGTTCGTGTCAACAATACACATGTGTTCATCAAGCCAAAATGAAGCTGTGGACGCTGGTTTGAACGAAAAGCTCAAAGAAAAGAAAAACAGAGAG    300
SH                                    CCATG
                                        G
     LeuValArgValAsnAsnThrHisValPheHisGlnAlaLysAsnGluAlaAlaValAspAlaGlyLeuAsnGluLysLeuLysGluLysGlnArgG
     L   V   R   V   N   N   T   H   V   F   H   Q   A   K   N   E   A   V   D   A   G   L   N   E   K   L   K   E   K   Q   R   E

LG 301 AGAAAGAAAAAGAAAACAAAAGAAAAAGAGAGAAAAAGATGATGCTAGTGACGGAAATGATGTTAACTAGCACAAAAACTGGAGAGAGAGATAGAGATGT    400
SH
     luLysGluLysGlnLysGluLysAspAspAlaSerAspGlyAsnAspValLeuThrSerThrLysThrGlyGluArgArgAspVa
     K   E   K   Q   K   E   K   D   D   A   S   D   G   N   D   V   L   T   S   T   K   T   G   E   R   D   R   D   V
```

FIG. 3B

```
LG  401  CAATGTTGGAACTAGTGGGACTTTCACTATTCCAAGGATTAAACCATTCAATGATAAAGATGATTTTACCGAGAATTAAGGGAAAAACTGTCCTTAATTTA   500
         l AsnValGlyThrSerGlyThrPheThrIleProArgIleLysProAsnAspLysMetIleLeuProArgIleLysGlyLysThrValLeuAsnLeu
SH                 N   V   G   T   S   G   T   F   T   I   P   R   I   K   P   F   N   D   K   M   I   L   P   R   I   K   G   K   T   V   L   N   L

LG  501  AATCATCTTCTTCAGTATAATCCGCAACAAATTGACATTTCGAACACTCGTGCCACTCAGTCACAAATTTGAAAAATGGCACGAGGAGTGAGGAATGATT   600
         AsnHisLeuLeuGlnTyrAsnProGlnGlnIleAspIleSerAsnThrArgAlaThrGlnSerGlnPheGluLysTrpHisGluGlyValArgAsnAspT
SH                 N   H   L   L   Q   Y   N   P   Q   Q   I   D   I   S   N   T   R   A   T   Q   S   Q   F   E   K   W   H   E   G   V   R   N   D   Y

LG  601  ATGGCCTGAATGATAAAGAGATGGAAGTAATGCTTAATGGTTTGATGGTTTGCATTGAGAATGGTACATCTCCGGACATATCTGGTGTGTCTGGGTTAT   700
         yrGlyLeuAsnAspLysGluMetGluValMetLeuAsnGlyLeuMetValTrpCysIleGluAsnGlyThrSerProAspIleSerGlyValTrpValMe
SH                 G   L   N   D   K   E   M   E   V   M   L   N   G   L   M   V   W   C   I   E   N   G   T   S   P   D   D   I   S   G   V   W   V   M

LG  701  GATGGATGATACTACAGGAACCCAAGTTGATTATCCAATCAAGCCTTTAATTGAGCATGCTACTCCGTCATTAGGCAATTATGGCTCACTTTAGTAAC   800
         tMetAspAspThrThrGlyThrGlnValAspTyrProIleLysProLeuIleGluHisAlaThrProSerPheArgGlnIleMetAlaHisPheSerAsn
SH                 M   D   D   T   T   G   T   Q   V   D   Y   P   I   K   P   L   I   E   H   A   T   P   S   F   R   Q   I   M   A   H   F   S   N

LG  801  GCGGCAGAAGCATACATTGCAAGGAGAAATGCTACTGAGAGGTACATGCCCGGTATGAATCAAGAGAAATTTGACTGACATTAGCCTCGCTAGATACG   900
         AlaAlaGluAlaTyrIleAlaArgArgAsnAlaThrGluArgTyrMetProArgTyrGlyIleLysArgAsnLeuThrAspIleSerLeuAlaArgTyrA
SH                 A   A   E   A   Y   I   A   R   R   N   A   T   E   R   Y   M   P   R   Y   G   I   K   R   N   L   T   D   I   S   L   A   R   Y   A
```

FIG. 3C

```
LG  901  CTTTCGATTTCTATGAGGTTAATTCGAAAACACCTGATAGGGCTCGCGAAGCTCGCATGCAGATGAAAGCTGCAGCGCTGCGAAACACTAATGCGAGAAT   1000
SH                laPheAspPheTyrGluValAsnSerLysThrProAspArgAlaArgGluAlaArgMetGlnMetLysAlaAlaAlaAlaLeuArgAsnThrAsnArgArgMe
                   F  D  F  Y  E  V  N  S  K  T  P  D  R  A  R  E  A  R  M  Q  M  K  A  A  A  A  L  R  N  T  N  R  R  M
                                                                                 A

LG 1001  GTTTGGTATGGACGGCAGTGTCAGTAACAAGGAAGAAAATACGGAGAGAGACACAGTGGAAGATGTCAATAGAGACATGCACTCTCCTGGGTATGCGC   1100
SH                tPheGlyMetAspGlyGlySerValSerAsnLysGluGluAsnThrGluArgHisThrValGluAspValAsnArgAspMetHisSerLeuLeuGlyMetArg
                   F  G  M  D  G  S  V  S  N  K  E  E  N  T  E  R  H  T  V  E  D  V  N  R  D  M  H  S  L  L  G  M  R
                                                                                                          NcoI .
LG 1101  AACTGAATACTCGCGCTTGTCGTGTTTGTCGAGTCTAACTCGACCCTGTTTCACCCCATGG   1160
SH                AsnEndIleLeuAlaAlaLeuValCysLeuSerSerLeuThrArgProCysPheThrProTrp
                   N  *  I  L  A  L  V  C  L  S  S  L  T  R  P  C  F  T  P  W

GAGCTGGGACAAAGTGGGTACCATGATATATTCCTAGGCTTATG<----3' RMM385
```

FIG. 4A

```
                                                                                                                        300
Australiancp-W  ..........  ..........  ..........  ..........  ..........  ..........  ..........  ..........
     Hacp-P    GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
     Usacp-P   GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
     Usacp-W   GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
     Fla831cp-W ..........  ..........  .CCATGGCTC  CATTCAATGA  GCTGGCGAAA  CAAGGGAGGG  CCCCATACGT  CTCGGAAGTT  GGATTAAGAA  GGTTGTATAC 400
Australiancp-W  ..........  ..........  ..........  ..........  ..........  ..........  ..........  ..........  ..........  ..........
     Hacp-P    AAGTGAACGT  GGATCAATGG  ACGAATTAGA  AGCGTATATA  GATAAATACT  TTGAGCGTGA  GAGAGGAGAC  TCGCCCGAAT  TACTAGTGTA  CCATGAATCA
     Usacp-P   AAGTGAACGT  GGATCAATGG  ACGAATTAGA  AGCGTATATA  GATAAATACT  TTGAGCGTGA  GAGAGGAGAC  TCGCCCGAAT  TACTAGTGTA  CCATGAATCA
     Usacp-W   AAGTGAACGT  GGATCAATGG  ATGAATTAGA  AGCGTATATA  GATAAATACT  TTGAGCGTGA  GAGAGGAGAC  TCACCCGAAT  TACTAGTGTA  CCATGAATCA
     Fla831cp-W GTGTGAACGC  GGATCAGTGG  ATGAATTGGA  AGCGTATATA  GATAAATATT  TTGAGCGTGA  GAGGGAGAC   TCACCCGAAG  TACTGGTGTA  CCATGAATCA 500
Australiancp-W  ..........  ..........  ..........  ..........  ..........  ..........  ..........  ..........  ..........  ..........
     Hacp-P    AGGGGCACTG  ATGATTATCA  ACTTGTTTGT  AGCAACAATA  CGCATGTGTT  TCATCAGTCC  AAGAATGAAG  CTGTGGATGC  TGGTTTGAAC  GAAAAGCTCA
     Usacp-P   AGGAGCACTG  ATGATTATCA  ACTTGTTTGT  AGCAACAATA  CGCATGTGTT  TCATCAGTCC  AAGAATGAAG  CTGTGGATGC  TGGTTTGAAT  GAAAACTCA
     Usacp-W   AGGAGCACTG  ATGATTATCA  ACTTGTTTGC  AGTAACAATA  CACATGTGTT  TCATCAGTGA  AAAAATGAAG  CTGTGGATAC  TGGTTTGAAT  GAAAATTCA
     Fla831cp-W AGGAGTACTG  ATGATTATGA  ACTTGTTTCG  GTCAACAATA  CACATGTGTT  TCATCAAGCC  AAAAATGAAG  CTGTGGACGC  TGGTTGACGC  GAAAAGCTCA 600
Australiancp-W  AAGAAAAAGA  AAAACAGAAA  GAAAAAGAAA  GAAAAAAACA  AAAAGAGAAA  GAGAAAGAGACG  ATGCTAGTGA  CGGAAATGAT  GTGTCAACTA  GCACAAAAAC
     Hacp-P    AAGAGAAGGA  AAAACAGAAA  GAAAAGAAGA  GAAAAAAACA  AAAAGAGAAA  GAAAAGACG   GTGCTAGTGA  CGGAAATGAT  GTGTCAACTA  GCACAAAAAC
     Usacp-P   AAGAGAAGGA  AAATCAGAAA  GAAAAAGAAA  GAAAAAAACA  AAAAGAGAAA  GAAAAGACG   GTGCTAGTGA  CGGAAATGAT  GTGTCAACTA  GCACAAAAAC
     Usacp-W   AAGAAAAGGA  AAAACAGAAA  GAAAAAGAAA  AAGAAAAACA  AAAAGAGAAA  GAAAAGACG   ATGCTAGTGA  CGGAAATGAT  GTGTCAACTA  GCACAAAAAC
     Fla831cp-W AAGAAAAAGA  GAGAACAGAGA AAGAAAAGAAA AAGAAAAACA AAAGAGAAA    GAAAAAGATG  ATGCTAGTGA  CGGAAATGAT  GTGTTAACTA  GCACAAAAAC
```

FIG. 4B

```
              601
Australiancp-W TGGAGAGAGA GATAGAGATG TCAATGTTGG GACCAGTGGA ACTTTCACTG TTCCAAGAAT CAAATCATTT ACTGACAAGA TGATTCTACC AAGAATTAAG
       Hacp-P TGGAGAGAGA GATAGAGATG TCAATGTTGG GACCAGTGGA ACTTTCACTG TTCCGAGAAT TAAATCATTT ACTGATAAGA TGGTTCTACC GAGAATTAAG
      Usacp-P TGGAGAGAGA GATAGAGATG TCAATGTTGG GACCAGTGGA ACTTTCACTG TTCCGAGAAT TAAATCATTT ACTGATAAGA TGGTTCTACC GAGAATTAAG
      Usacp-W TGGAGAGAGA GATAGAGATG TCAATGTTGG GACCAGTGGA ACTTTCACTG TTCCGAGAAT TAAATCATTT ACTGATAAGA TGATTCTACC GAGAATTAAG
    Fla831cp-W TGGAGAGAGA GATAGAGATG TCAATGTTGG AACTAGTGGG ACTTTCACTA TTCCAAGGAT TAAACCATTC AATGATAAGA TGATTTACC GAGAATTAAG
              701                                                                                                    800
Australiancp-W GGAAAGACTG TCCTTAATTT AAATCACCTT CTTCAGTATA ACCCGCAACA AATTGACATT TCTAACACTC GTGCCACTCA GTCACAATTT GAGAAGTGGT
       Hacp-P GGGAAGACTG TCCTTAATTT AAATCATCTT CTTCAGTACA ATCCGCAACA AATTGACATT TCTAACACTC GTGCCACTCA TTCACAATTT GAGAAGTGGT
      Usacp-P GGGAAGACTG TCCTTAATTT AAATCATCTT CTTCAGTACA ATCCGCAACA AATTGACATT TCTAACACTC GTGCCACTCA TTCACAATTT GAGAAGTGGT
      Usacp-W GGAAAGTCTG TCCTTAATTT AAATCACCTA CTTCAGTATA ATCCGCAACA AATTGACATT TCTAACACTC GTGCCACTCA GTCACAATTT GAGAAGTGGT
    Fla831cp-W GGAAAAACTG TCCTTAATTT AAATCATCTT CTTCAGTATA ATCCATCATT TCGAACACTC GTGCCACTCA GTCACAATTT GAAAAATGGC
              801                                                                                                    900
Australiancp-W ATGAGGGAGT GAGGAATGAT TATGGCCTTA ATGATAATGA AATGCAAGTG ATGCTAAATG GCTTGATGGT TTGGTGTATC GAGAATGGTA CATCTCCAGA
       Hacp-P ATGAGGGAGT GAGGAATGAT TATGGCCTTA ATGATAATGA AATGCAAGTG ATGCTAAATG GTTTGATGGT TTGGTGTATC GAGAATGGTA CATCTCCAGA
      Usacp-P ATGAGGGAGT GAGGAATGAT TATGGCCTTA ATGATAATGA AATGCAAGTG ATGCTAAATG GTTTGATGGT TTGGTGTATC GAGAATGGTA CATCTCCAGA
      Usacp-W ATGAGGGAGT GAGGAATGAT TATGGCCTTA ATGATAATGA AATGCAAGTG ATGCTAAATG GTTTGATGGT TTGGTGTATC GAGAATGGTA CATCTCCAGA
    Fla831cp-W ACGAGGGAGT GAGGAATGAT TATGGCCTGA ATGATAAAGA GATGGAAGTA ATGTTAAATG GCTTGATGGT TTGGTGTATT GAGAATGGTA CATCTCCGGA
              901                                                                                                   1000
Australiancp-W CATATCTGGT GTCTGGGTTA TGATGGATG. .....GGGAA ACCCAAGTTG ATTATCCAAT CAAGCCTTTA ATTGAGCATG CTACTCCGAC ATTTAGGCAA
       Hacp-P CATATCTGGT GTCTGGGTTA TGATGGATG. .....GGGAA ACCCAAGTTG ATTATCCAAT CAAGCCTTTG ATTGAGCATG CTACTCCGTC ATTTAGGCAA
      Usacp-P CATATCTGGT GTCTGGGTTA TGATGGATG. .....GGGAA ACCCAAGTTG ATTATCCAAT CAAGCCTTTG ATTGAGCATG CTACTCCGTC ATTTAGGCAA
      Usacp-W CATATCTGGT GTCTGGGTTA TGATGGATG. .....GGGAA ACCCAAGTTG ATTATCCAAT CAAGCCTTTA ATTGAGCATG CTACTCCGTC ATTTAGGCAA
    Fla831cp-W CATATCTGGT GTCTGGGTTA TGATGGATGA TACTACAGGA ACCCAAGTTG ATTATCCAAT CAAGCCTTTA ATTGAGCATG CTACTCCGTC ATTTAGGCAA
                                             INSERTION
```

FIG. 4C

```
              1001                                                                                                    1100
Australiancp-W ATTATGGCTC ACTTTAGTAA TCCGGCAGAA GCATATATTG CAAAGAGAAA TGCTACTGAG AGATACATGC CGCGGTATGG AATCAAGAGA AATTTGACTG
       Hacp-P ATTATGGCTC ACTTTAGTAA CGCGGCAGAA GCATACATTG CGAAGAGAAA TGCTACTGAG AGTTACATGC CGCGGTATGG AATCAAGAGA AATTTGACTG
       Usacp-P ATTATGGCTC ACTTTAGTAA CGCGGCAGAA GCATACATTG CGAAGAGAAA TGCTACTGAG AGTTACATGC CGCGGTATGG AATCAAGAGA AATTTGACTG
       Usacp-W ATTATGGCTC ACTTTAGTAA CGCGGCAGAA GCATACATTG CGAAAAGAAA TGCTACTGAG AGTTACATGC CGCGGTATGG AATCAAGAGA AATTTGACTG
     Fla831cp-W ATTATGGCTC ACTTTAGTAA CGCGGCAGAA GCATACATTG CAAGGAGAAA TGCTACTGAG AGTTACATGC CGCGGTATGG AATCAAGAGA AATTTGACTG 1101                                                                                                    1200
Australiancp-W ACATTAGCCT CGCCAGATAC GCTTTCGATT TCTATGAGGT GAATTCGAAA ACACCTGATA GGGCTCGCGA AGTCACATG CAGATGAAAG CTGCAGCGCT
       Hacp-P ACATTAGCCT CGCTAGATAC GCTTTCGACT TCTATGAGGT GAATTCGAAA ACACCTGATA GGGCTCGCGA AGTCACATG CAGATGAAGG CTGCAGCGCT
       Usacp-P ACATTAGCCT CGCTAGATAC GCTTTCGACT TCTATGAGGT GAATTCGAAA ACACCTGATA GGGCTCGCGA AGTCACATG CAGATGAAGG CTGCAGCGCT
       Usacp-W ACATTAGCCT CGCTAGATAC GCTTTCGACT TCTATGAGGT GAATTCGAAA ACACCTGATA GGGCTCGCGA AGCCACATG CAGATGAAGG CTGCAGCACT
     Fla831cp-W ACATTAGCCT CGCTAGATAC GCTTTCGATT TCTATGAGGT TAATTCGAAA ACACCTGATA GGGCTCGCGA AGTCGCCATG CAGATGAAAG CTGCAGCGCT 1201                                                                                                    1300
Australiancp-W GCGAAACACT AGTCGCAGAA TGTTTGGTAT GGACGGCAGT GTTAGTAACA AGGAAGAAAA CATGAGAGA AAGATGTCAA TAGAGACATG
       Hacp-P GCGAAACACC AGTCGCAGAA TGTTTGGTAT GGACGGCAGT GTTAGTAACA AGGAAGAAAA CACGAGAGA AAGATGTCAA TAGAGACATG
       Usacp-P GCGAAACACC AGTCGCAAAA TGTTTGGTAT GGACGGCAGT GTTAGTAACA AGGAAGAAAA CACGAGAGA AAGATGTCAA TAGAGACATG
       Usacp-W GCGAAACACT AGTCGCCAGA TGTTTGGTAT GGACGGCAGT GTTAGTAACA AGGAAGAAAA CACGGAGAGA AAGACGTCAA TAGAGACATG
     Fla831cp-W GCGAAACACT AATCGCAGAA TGTTTGGTAT GGACGGCAGT GTCAGTAACA AGGAAGAAAA TACGAGAGA AAGATGTCAA TAGAGACATG 1301                                                                                                    1400
Australiancp-W CACTCTCTCC TGGGTATGCG CAACTGAATA CTCGCACTTG TGTGTTTGTC GGGCCTGGCT CGACCTTGTT TCACCTTATA GTACTATATA AGCATTAGAA
       Hacp-P CACTCTCTCC TGGGTATGCG CAACTAAATA CCTGCGCTTG TGTGTTTGTT GAGTCTGACT CGACCTGTT TCACTTTATG GTACTATATA AGCATTAGAA
       Usacp-P CACTCTCTCC TGGGTATGCG CAACTAAATA CCTGCGCTTG TGTGTTTGTT GAGTCTGACT CGACCCTGTT TCACCTTATG GTACTATATA AGCATTAGAA
       Usacp-W CACTCTCTCC TGGGTATGCG CAACTAAATA CTTGCGCTTG TGTGTTTGTC GAGCTTGACT CGACCCTGTT TCACCTTATG GTACTATATA AGCATTAGAA
     Fla831cp-W CACTCTCTCC TGGGTATGCG CAACTGAATA CTCGCGCTTG TGTGTTTGTC GAGTCTAACT CGACCTGTT TCACCCATG G..........
```

FIG. 5A

```
                 1
      Hacp-P     RNKQNLWFMS HRGILIDDIY IPKLEPERIV AILEWDKSKL PEHRLEAITA AMIESWGYGD LTHQIRRFYQ WLEQAPFNE  LAKQGRAPYV SEVGLRRLYT    100
      Usacp-P    .......... .......... .......... .......... .......... .......... LTHQIRRFYQ WLEQAPFNE  LAKQGRAPYV SEVGLRRLYT
      Usacp-W    .......... .......... .......... .......... .......... ...ITA AMIESWGYGD LTHQIRRFYQ WLEQAPFNE  LAKQGRAPYV SEVGLRRLYT
      Fla831cp-W .......... .......... .......... .......... .......... .......... .......... .vleqAPFNE  LAKQGRAPYV SEVGLRRLYT
      Australiancp-W .......... .......... .......... .......... .......... .......... .......... .......... .......... ..........
                                                                                                      LONG

*101                                               *                              *                      *     * 200
      Hacp-P     SERGSMDELE AYIDKYFERE RGDSPELLVY HESRGTDDYQ LVCSNNTHVF HQSKNEAVDA GLNEKLKEKE KQKEKEKEKQ KEKEKDGASD GNDVSTSTKT
      Usacp-P    SERGSMDELE AYIDKYFERE RGDSPELLVY HESRSTDDYQ LVCSNNTHVF HQSKNEAVDA GLNEKLKEKE NQKEKEKEKQ KEKEKDGASD GNDVSTSTKT
      Usacp-W    SERGSMDELE AYIDKYFERE RGDSPELLVY HESRSTDDYQ LVCSNNTHVF HQSKNEAVDT GLNEKFKEKE KQKEKEKEKQ KEKEKDDASD GNDVSTSTKT
      Fla831cp-W SERGSVDELE AYIDKYFERE RGDSPEVLVY HESRSTDDYE LVRVNNTHVF HQAKNEAVDA GLNEKLKEKE KQREKEKEKQ KEKEKDDASD GNDVLTSTKT
      Australiancp-W CERGSVDELE .......... .......... .......... ..VF HQSKNEAVDA GLNEKLKEKE KQKEKEKEKQ KEKEKDDASD GNDVSTSTKT
                 1     2         3          4 5 6       7                                                                     8
                                                          SHORT 201                                                        *                              *       ***      300
      Hacp-P     GERDRDVNVG TSGTFTVPRI KSFTDKMVLP RIKGKTVLNL NHLLQYNPQQ IDISNTRATH SQFEKWYEGV RNDYGLNDNE MQVMLNGLMV WCIENGTSPD
      Usacp-P    GERDRDVNVG TSGTFTVPRI KSFTDKMVLP RIKGKTVLNL NHLLQYNPQQ IDISNTRATH SQFEKWYEGV RNDYGLNDNE MQVMLNGLMV WCIENGTSPD
      Usacp-W    GERDRDVNVG TSGTFTVPRI KSFTDKMILP RIKGKSVLNL NHLLQYNPQQ IDISNTRATQ SQFEKWYEGV RNDYGLNDNE MQVMLNGLMV WCIENGTSPD
      Fla831cp-W GERDRDVNVG TSGTFTIPRI KPFNDKMILP RIKGKTVLNL NHLLQYNPQQ IDISNTRATQ SQFEKWHEGV RNDYGLNDKE MEVMLNGLMV WCIENGTSPD
      Australiancp-W GERDRDVNVG TSGTFTVPRI KSFTDKMILP RIKGKTVLNL NHLLQYNPQQ IDISNTRATQ SQFEKWYEGV RNDYGLNDNE MQVMLNGLMV WCIENGTSPD
                        9                                                              10              11 12
```

FIG. 5B

```
            301         *    ***                                    *                                                400
   Hacp-P   ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
   Usacp-P  ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
   Usacp-W  ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
   Fla83lcp-W ISGVWVMMDD TTGTQVDYPI KPLIEHATPS FRQIMAHFSN AAEAYIAKRN ATERYMPRYG IKRNLTDISL ARYAFDFYEV NSKTPDRARE AHMQMKAAAL
   Australiancp-W ISGVWVMMDG ..ETQVDYPI KPLIEHATPT FRQIMAHFSN AAEAYIARRN ATERYMPRYG IKRNLTDISL ARYAFDFYEV NSKTPDRARE ARMQMKAAAL
                       13 INSERTION                                  14

401*                                          *
   Hacp-P   RNTSRRMFGM DGSVSNKEEN TERHTVEDVN RDMHSLLGMR N*
   Usacp-P  RNTSRKMFGM DGSVSNKEEN TERHTVEDVN RDMHSLLGMR N*
   Usacp-W  RNTSRRMFGM DGSVSNKEEN TERHTVEDVN RDMHSLLGMR N*
   Fla83lcp-W RNTNRRMFGM DGSVSNKEEN TERHTVEDVN RDMHSLLGMR N*
   Australiancp-W RNTSRRMFGM DGSVSNKEEN MERHTVEDVN RDMHSLLGMR N*
```

FIG. 8A

```
              201                                                                                           300
Fla831cpW     ..........  ..........  .CCATGGCTC  CATTCAATGA  GCTGGCGAAA  CAAGGGAGGG  CCCCATACGT  CTCGGAACTT  GGATTAAGAA  GGTTGTATAC
HacpP         GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
UsacpP        GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
UsacpW        GATTTTACCA  ATGGGTTCTT  GAGCAAGCTC  CATTCAATGA  GTTGGCGAAA  CAAGGAAGGG  CCCCATACGT  CTCGGAAGTT  GGATTAAGAA  GATTGTACAC
Australiancpw ..........  ..........  ..........  ..........  ..........  ..........  ..........  ..........  ..........  ..........
BrazilcpP     ..........  ..........  ..........  ..........  ..........  ..........  ..........  ..........  ..........  ..........
YkcpP         ..........  .agcaggctc  cattcaatga  attagcgaag  caggcaggg   ctccatatgt  gtctgaggtt  ggattgaggc  gcttatacac 301                                                                                           400
Fla831cpW     GTGTGAACGC  GGATCAGTGG  ATGAATTGGA  AGCGTATATA  GATAAATATT  TTGAGCGTGA  GAGGGGAGAC  TCACCCGAAG  TACTGGTGTA  CCATGAATCA
HacpP         AAGTGAACGT  GGATCAATGG  ACGAATTAGA  AGCGTATATA  GATAAATACT  TTGAGCGTGA  GAGAGGAGAC  TCGCCCGAAT  TACTAGTGTA  CCATGAATCA
UsacpP        AAGTGAACGT  GGATCAATGG  ACGAATTAGA  AGCGTATATA  GATAAATACT  TTGAGCGTGA  GAGAGGAGAC  TCGCCCGAAT  TACTAGTGTA  CCATGAATCA
UsacpW        AAGTGAACGT  GGATCAATGG  ATGAATTAGA  AGCGTATATA  GATAAATACT  TTGAGCGTGA  GAGAGGAGAC  TCACCCGAAT  TACTAGTGTA  CCATGAATCA
Australiancpw ..........  ..........  ..........  ..........  ..........  ..........  ..........  ..........  ..........  ..........
BrazilcpP     ..........  ..........  ..........  ..........  ..........  ..........  ..........  ..........  ..........  ..........
YkcpP         tagtaagcgt  gggtcaatgg  atgaattgga  ggcctacata  gataaatatt  ttgaacgaga  gagaggagac  tcacccgaat  tactagtgta  ccatgaatcg 401                                                                                           500
Fla831cpW     AGGAGTACTG  ATGATTATGA  ACTTGTTCGT  GTCAACAATA  CACATGTGTT  TCATCAAGCC  AAAAATGAAG  CTGTGGACGC  TGGTTTGAAC  GAAAAGCTCA
HacpP         AGGGGCACTG  ATGATTATCA  ACTTGTTTGT  AGCAACAATA  CGCATGTGTT  TCATCAGTCA  AAGAATGAAG  CTGTGGATGC  TGGTTTGAAT  GAAAAACTCA
UsacpP        AGGAGCACTG  ATGATTATCA  ACTTGTTTGT  AGCAACAATA  CGCATGTGTT  TCATCAGTCA  AAGAATGAAG  CTGTGGATGC  TGGTTTTGAAT  GAAAAACTCA
UsacpW        AGGAGCACTG  ATGATTATCA  ACTTGTTTGC  AGTAACAATA  CACATGTGTT  TCATCAGTCA  AAAAATGAAG  CTGTGGATAC  TGGTTTGGAT  GAAAAATTCA
Australiancpw ..........  ..........  ..........  ..........  ..........  ......TCC   AAAAATGAAG  CTGTGGATGC  TGGTTTGAAT  GAAAAGCTCA
BrazilcpP     ..........  ..........  ..........  ..........  ..........  ...CCATGG   CCATGG      CTGTGGATGC  TGGTTTGAAT  GAAAAGCGTA
YkcpP         agaagcactg  acaatcatca  attaacccgc  ggcagtaata  cacatgtgtt  tcaccagtct  aaaaatgaag  ctgtggatac  cggtctgaat  gagaagctca 501                                                                                           600
Fla831cpW     AAGAAAAAGA  AAAACAGAGA  GAGAAGAAAA  AAAAGAGAAA  AAAAGAGACG  GAAAAAGATG  ATGCTAGTGA  CGGAAATGAT  GTGTTAACTA  GCACAAAAAC
HacpP         AAGAGAAGGA  AAAACAGAAA  GAGAAGAAAA  AAAAGAGAAA  AAAAGAGACG  GAAAAAGACG  GTGCTAGTGA  CGGAAATGAT  GTGTCAACTA  GCACAAAAAC
UsacpP        AAGAGAAGGA  AAATCAGAAA  GAGAAGAAAA  AAAAGAGAAA  AAAAGAGACG  GAAAAAGACG  GTGCTAGTGA  CGGAAATGAT  GTGTCAACTA  GCACAAAAAC
UsacpW        AAGAAAAGGA  AAAACAGAAA  GAGAAGAAAA  AAAAGAGAAA  AAAAGAGACG  GAAAAAGACG  ATGCTAGTGA  CGGAAATGAT  GTGTCAACTA  GCACAAAAAC
Australiancpw AAGAAAAAGA  AAAACAGAAA  GAGAAGAAAA  AAAAGAGAAA  AAAAGAGACG  GAAAAAGACG  ATGCTAGTGA  CGGAAATGAT  GTGTCAACTA  GCACAAAAAC
BrazilcpP     AAGAACAAGA  GAAACAAGAA  GAAAAG....  ..........  AAGAAGAAAA  GAGAAGAAAA  GAGAAAGACG  CGGAAACGAT  GTGTCAACTA  GCACAAGAAC
YkcpP         aagaaaaaga  aagcagaaa   aagataaaca  aagataaaca  acaagataaa  gacaatgatg  gagctagtga  cggaaacgat  gtgtcaacta  gcacaaaaac
```

FIG. 8B

```
              601
Fla83lcpW     TGGAGAGAGA GATAGAGATG TCAATGTTGG AACTAGTGGG ACTTTCACTA TTCCAAGGAT TAAACCATTC AATGATAAGA TGATTTTACC GAGAATTAAG
HacpP         TGGAGAGAGA GATAGAGATG TCAATGTTGG GACCAGTGGA ACTTTCACTG TTCCGAGAAT TAAATCATTT ACTGATAAGA TGGTTCTACC GAGAATTAAG
UsacpP        TGGAGAGAGA GATAGAGATG TCAATGTTGG GACCAGTGGA ACTTTCACTG TTCCGAGAAT TAAATCATTT ACTGATAAGA TGGTTCTACC GAGAATTAAG
UsacpW        TGGAGAGAGA GATAGAGATG TCAATGTTGG GACCAGTGGA ACTTTCACTG TTCCGAGAAT TAAATCATTT ACTGATAAGA TGATTCTACC GAGAATTAAG
AustraliancpW TGGAGAGAGA GATAGAGATG TCAATGTTGG GACCAGTGGA ACTTTCACTG TTCCGAGAAT CAAATCATTT ACTGACAAGA TGATTCTACC AAGAATTAAG
BrazilcpP     TGGAGAGAGA GACAGAGATG TCAATGTTGG GACCAGTGGA ACTTTCACTG TTCCGAGAAC AAAATCATTT ACTGATAAGA TGATTTTACC TAGAATTAAG
YkcpP         tggagagaga gataggatg tcaatgccgg aactagtgga accttcactg ttccggat aaagtcattt actgataaga tgatcttacc aagaattaag 701
Fla83lcpW     GGAAAAACTG TCCTTAATTT AAATCATCTT CTTCAGTATA ATCCGCAACA AATTGACATT TCGAACACTC GTGCCACTCA GTCACAATTT GAAAAATGGC
HacpP         GGGAAGACTG TCCTTAATTT AAATCATCTT CTTCAGTACA ATCCGCAACA AATTGACATT TCTAACACTC GTGCCACTCA TTCACAATTT GAGAAGTGGT
UsacpP        GGGAAGACTG TCCTTAATTT AAATCATCTT CTTCAGTACA ATCCGCAACA AATTGACATT TCTAACACTC GTGCCACTCA TTCACAATTT GAGAAGTGGT
UsacpW        GGAAAGTCTG TCCTTAATTT AAATCACCTA ATCCGCAACA AATTGACATT TCTAACACTC GTGCCACTCA GTCACAATTT GAGAAGTGGT
AustraliancpW GGAAAGACTG TCCTTAATTT AAATCACCTT CTTCAGTATA ACCCGCAACA AATTGACATT TCTAACACTC GTGCCACTCA GTCACAATTT GAGAAGTGGT
BrazilcpP     GGAAAAACTG TCCTTAATTT AAATCATCTG ATTCAGTATA ATCCGCAACA AATTGACATT TCTAACACTC GTGCTACTCA ATCACAATTT GAGAAGTGGT
YkcpP         ggaaaaactg tccttaattt aaatcatctt cttcagtata atccgaaaca agttgacatc tcaaacactc gcgccactca atctcaattt ggagaagtgt 801
Fla83lcpW     ACGAGGGAGT GAGGAATGAT TATGGCCTGA ATGATAATGA GATGGAAGTA AATGTTAAATG GCTTGATGGT TTGGTGTATT GAGAATGGTA CATCTCCGGA
HacpP         ATGAGGGAGT GTCTGGGTTA TATGGCCTTA ATGATAATGA ATGCAAGTG AATGTTAAATG GTTTGATGGT TTGGTGTATC GAGAATGGTA CATCTCCAGA
UsacpP        ATGAGGGAGT GTCTGGGTTA TATGGCCTTA ATGATAATGA ATGCAAGTG AATGCAAGTG ATGCTAAATG GTTTGATGGT TTGGTGTATC GAGAATGGTA CATCTCCAGA
UsacpW        ATGAGGGAGT GTCTGGGTTA TATGGCCTTA ATGATAATGA ATGCAAGTG ATGCTAAATG GTTTGATGGT TTGGTGTATC GAGAATGGTA CATCTCCAGA
AustraliancpW ATGAGGGAGT GTCTGGGTTA TATGGCCTTA ATGATAATGA ATGCAAGTG AATGCTAAATG GCTTGATGGT TTGGTGTATC GAGAATGGTA CATCTCCAGA
BrazilcpP     ATGAGGGAGT GTCTGGGTTA TATGGCCTTA ATGATAATGA ATGCAAGTG GTGCTAAATG GTTTGATGGT TTGGTGTATC GAAAACGGTA CATCTCCAGA
YkcpP         atgagggagt gagaaatgat tatggcctta atgataacga aatgcaagta atgttaaatg atgttaaatg gtttgatggt ttggtgtatc gaaaatggta catctccaga 901                                                                                                      1000
Fla83lcpW     CATATCTGGT GTCTGGGTTA TGATGGATGA TACTACAGGA ACCCAAGTTG ATTATCCAAT CAAGCCTTTA ATTGAGCATG CTACTCCGTC ATTTAGGCAA
HacpP         CATATCTGGT GTCTGGGTTA TGATGGATG. ......GGGAA ACCCAAGTTG ATTATCCAAT CAAGCCTTTG ATTGAGCATG CTACTCCGTC ATTTAGGCAA
UsacpP        CATATCTGGT GTCTGGGTTA TGATGGATG. ......GGGAA ACCCAAGTTG ATTATCCAAT CAAGCCTTTG ATTGAGCATG CTACTCCGTC ATTTAGGCAA
UsacpW        CATATCTGGT GTCTGGGTTA TGATGGATG. ......GGGAA ACCCAAGTTG ATTATCCAAT CAAGCCTTTA ATTGAGCATG CTACTCCGTC ATTTAGGCAA
AustraliancpW CATATCTGGT GTCTGGGTTA TGATGGATG. ......GGGAA ACCCAAGTTG ATTATCCAAT CAAGCCTTTA ATTGAGCATG CTACTCCGTC ATTTAGGCAA
BrazilcpP     ACGATCTGGT GTCTGGGTTA TGATGGATG. ......GGGAA ACCCAAGTTG ATTATCCAAT CAAGCCTTTA ATTGAGCATG CTACTCCGAC ATTTAGGCAA
YkcpP         CATATCTGGT GTCTGGGTTA TGATGGATG. ......GGGAA ACCCAGGTTG ACTATCCAAT CAAGCCTTTA ATTGAGCATG CTACTCCGTC GTTTAGGCAA
              tatatctggt gtctggtta tgatggatg. ......gggaa acccaagtcg attatcccat taaacctttg attgaacacg caactccttc atttaggcaa
```

FIG. 8C

```
              1001                                                                                                                1100
Fla831cpW     ATTATGGCTC ACTTTAGTAA CGCGGCAGAA GCATACATTG CAAGGAGAAA TGCTACTGAG AGTACATGC CGCGGTATGG AATCAAGAGA AATTTGACTG
HacpP         ATTATGGCTC ACTTTAGTAA CGCGGCAGAA GCATACATTG CGAAGAGAAA TGCTACTGAG AGTACATGC CGCGGTATGG AATCAAGAGA AATTTGACTG
UsacpP        ATTATGGCTC ACTTTAGTAA CGCGGCAGAA GCATACATTG CGAAGAGAAA TGCTACTGAG AGTACATGC CGCGGTATGG AATCAAGAGA AATTTGACTG
UsacpW        ATTATGGCTC ACTTTAGTAA CGCGGCAGAA GCATACATTG CGAAAAGAAA TGCTACTGAG AGTACATGC CGCGGTATGG AATCAAGAGA AATTTGACTG
AustraliancpW ATTATGGCTC ACTTTAGTAA TGCGGCAGAA GCATATATTG CAAAGAGAAA TGCTACTGAG AGATACATGC CGCGGTATGG AATCAAGAGA AATTTGACTG
BrazilcpP     ATTATGGCTC ATTTCAGTAA CGCGGCAGAA GCATACATTA CAAAGAGAAA TGCTACTGAG AGTACATGC CGCGGTATGG GATCAAGAGA AATTTGACTG
YkcpP         atcatgctc  acttcagtaa cgcggcagag gcatacatcg cgaaggagaa tgcaactgag aagtactgc  cgcggtatgg aatcaagaga aatttgactg
              1101                                                                                                                1200
Fla831cpW     ACATTAGCCT CGCTAGATAC GCTTTCGATT TCTATGAGGT TAATTCGAAA ACACCCTGATA GGGCTCGCCA AGCTCGCATG CAGATGAAAG CTGCAGCGCT
HacpP         ACATTAGCCT CGCTAGATAC GCTTTCGACT TCTATGAGGT GAATTCGAAA ACACCCTGATA GGGCTCGCCA AGCTCACATG CAGATGAAGG CTGCAGCGCT
UsacpP        ACATTAGCCT CGCTAGATAC GCTTTCGACT TCTATGAGGT GAATTCGAAA ACACCCTGATA GGGCTCGCCA AGCTCACATG CAGATGAAGG CTGCAGCGCT
UsacpW        ACATTAGCCT CGCTAGATAC GCTTTCGACT TCTATGAGGT GAATTCGAAA ACACCCTGATA GGGCTCGCCA AGCCCACATG CAGATGAAGG CTGCAGCGCT
AustraliancpW ACATTAGCCT CGCCAGATAC GCTTTCGATT TCTATGAGGT GAATTCGAAA ACACCCTGATA GGGCTCGCGA AGCTCGCATG CAGATGAAAG CTGCAGCGCT
BrazilcpP     ACATTAGTCT TGCTAGATAT GCTTTCGATT TCTATGAGGT GAATTCGAAA ACACCCTGATA GGGCTCGCGA AGCTCACATG CAGATGAAAG CTGCAGCGCT
YkcpP         acattagtct cgctagatat gctttcgatt tctatgaggt gaattcgaaa acacctgata gggctcgtga agctcatatg cagatgaagg ctgcagcgct
              1201                                                                                                                1300
Fla831cpW     GCGAAACACT AATCGCAGAA TGTTTGGTAT GGACGGCAGT GTCAGTAACA AGGAAGAAAA TACGGAGAGA CACACAGTGG AAGATGTCAA TAGAGACATG
HacpP         GCGAAACACC AGTCGCAGAA TGTTTGGTAT GGACGGCAGT GTTAGTAACA AGGAAGAAAA CACGGAGAGA CACACAGTGG AAGATGTCAA TAGAGACATG
UsacpP        GCGAAACACC AGTCGCAAAA TGTTTGGTAT GGACGGCAGT GTTAGTAACA AGGAAGAAAA CACGGAGAGA CACACAGTGG AAGATGTCAA TAGAGACATG
UsacpW        GCGAAACACT AGTCGCAGAA TGTTTGGTAT GGACGGCAGT GTTAGTAACA AGGAAGAAAA CACGGAGAGA CACACAGTGG AAGACGTCAA TAGAGACATG
AustraliancpW GCGAAACACT AGTCGCAGAA TGTTTGGTAT GGACGGCAGT GTTAGTAACA AGGAAGAAAA CATGGAGAGA CACGGAGAGA CACACAGTGG AAGAGTCAA TAGAGACATG
BrazilcpP     GCGAAACACT AATCGCAGAA TGTTTGGTAT GGACGGCAGT GTTAGTAACA AGGAAGAAAA CACGGAGAGA CACACAGTGG AAGATGTCAA TAGAGACATG
YkcpP         acgcaatact aatcgcaaaa tgtttggaat ggacggcagt gtcagtaaca aggaagaaaa aggaagaaaa aggaagaaaa cacacagtgg aagatgtcaa cagagacatg
              1301
Fla831cpW     CACTCTCTCC TGGGTATGCG CAACTGAATA CTCGCGCTTG TGTGTTTGTC GAGTCTAACT CGACCCTGTT TCACCCCATG G
HacpP         CACTCTCTCC TGGGTATGCG CAACTAAATA CCTGCGCTTG TGTGTTTGTT GAGTCTGACT CGACCCTGTT TCACCTTATG G
UsacpP        CACTCTCTCC TGGGTATGCG CAACTAAATA CCTGCGCTTG TGTGTTTGTT GAGTCTGACT CGACCCTGTT TCACCTTATG G
UsacpW        CACTCTCTCC TGGGTATGCG CAACTAAATA CTTGCGCTTG TGTGTTTGTT GAGTCTGACT CGACCCTGTT TCACCTTATG G
AustraliancpW CACTCTCTCC TGGGTATGCG CAACTGAATA CTCGCACTTG TGTGTTTGTC GGGCCTGGCT CGACCCTGTT TCACCCCATG G
BrazilcpP     CACTCTCTCC TGGGTATGCG CAACTGAATA CTCGCGCT.. GGTGCTTGTT GGGCCTGGCT CGACCCTGTT TCACCCCATG G
YkcpP         cactctctcc tgggtatgcg caattgaata ctcgcgctag tgtgtttgtc gggcctggct cgacctgtt  tcaccttata a
```

FIG. 9A

```
             1                                                                                              100
Fla831cpW    ..........  ..........  ..........  ..........  ..........  ....MAPFNE  LAKQGRAPYV  SEVGLRRLYT
HacpP        RNKQNLWFMS  HRGILILDDIY  IPKLEPERIV  AILEWDKSKL  PEHRLEAITA  AMIESWGYGD  LTHQIRRFYQ  WVLEQAPFNE  LAKQGRAPYV  SEVGLRRLYT
UsacpP       ..........  ..........  ..........  ..........  ..........  ..........  LTHQIRRFYQ  WVLEQAPFNE  LAKQGRAPYV  SEVGLRRLYT
UsacpW       ..........  ..........  ..........  ..........  ....ITA     AMIESWGYGD  LTHQIRRFYQ  WVLEQAPFNE  LAKQGRAPYV  SEVGLRRLYT
YkcpP        ..........  ..........  ..........  ..........  ..........  ..........  ..........  ...EQAPFNE  LAKQGRAPYV  SEVGLRRLYT
AustraliancpW ..........  ..........  ..........  ..........  ..........  ..........  ..........  ..........  ..........  ..........
BrazilcpP    ..........  ..........  ..........  ..........  ..........  ..........  ..........  ..........  ..........  ..........

101                                                                                            200
Fla831cpW    CERGSVDELE  AYIDKYFERE  RGDSPEVLVY  HESRSTDDYE  LVRVNNTHVF  HQAKNEAVDA  GLNEKLKEKE  KQREKEKEKQ  KEKEKDDASD  GNDVLTSTKT
HacpP        SERGSMDELE  AYIDKYFERE  RGDSPELLVY  HESRGTDDYQ  LVCSNNTHVF  HQSKNEAVDA  GLNEKLKEKE  KQKEKEKEKQ  KEKEKDGASD  GNDVSTSTKT
UsacpP       SERGSMDELE  AYIDKYFERE  RGDSPELLVY  HESRSTDDYQ  LVCSNNTHVF  HQSKNEAVDA  GLNEKLKEKE  NQKEKEKEKQ  KEKEKDGASD  GNDVSTSTKT
UsacpW       SERGSMDELE  AYIDKYFERE  RGDSPELLVY  HESRSTDDYQ  LVCSNNTHVF  HQSKNEAVDT  GLNEKFKEKE  KQKEKEKEKQ  KEKEKDDASD  GNDVSTSTKT
YkcpP        SKRGSMDELE  AYIDKYFERE  RGDSPELLVY  HESRSTDNHQ  LTRGSNTHVF  HQSKNEAVDT  GLNEKLKEKE  KQKEKEKDKQ  QDKDNDGASD  GNDVSTSTKT
AustraliancpW ..........  ..........  ..........  ..........  ..........  ..SKNEAVDA  GLNEKLKEKE  KQKEKEKEKQ  KEKEKDDASD  GNDVSTSTKT
BrazilcpP    ..........  ..........  ..........  ..........  ..........  ....MAVDA   GLNEKRKEQE  KQEEKE_EKQ  KKKEKDDASY  GNDVSTSTRT 201                                                                                            300
Fla831cpW    GERDRDVNVG  TSGTFTIPRI  KPFNDKMILP  RIKGKTVLNL  NHLLQYNPQQ  IDISNTRATQ  SQFEKWHEGV  RNDYGLNDKE  MEVMLNGLMV  WCIENGTSPD
HacpP        GERDRDVNVG  TSGTFTVPRI  KSFTDKMVLP  RIKGKTVLNL  NHLLQYNPQQ  IDISNTRATH  SQFEKWYEGV  RNDYGLNDNE  MQVMLNGLMV  WCIENGTSPD
UsacpP       GERDRDVNVG  TSGTFTVPRI  KSFTDKMVLP  RIKGKTVLNL  NHLLQYNPQQ  IDISNTRATH  SQFEKWYEGV  RNDYGLNDNE  MQVMLNGLMV  WCIENGTSPD
UsacpW       GERDRDVNVG  TSGTFTVPRI  KSFTDKMILP  RIKGKSVLNL  NHLLQYNPQQ  IDISNTRATQ  SQFEKWYEGV  RNDYGLNDNE  MQVMLNGLMV  WCIENGTSPD
YkcpP        GERDRDVNAG  TSGTFTVPRI  KSFTDKMILP  RIKGKTVLNL  NHLLQYNPKQ  VDISNTRATQ  SQFEKWYEGV  RNDYGLNDNE  MQVMLNGLMV  WCIENGTSPD
AustraliancpW GERDRDVNVG  TSGTFTVPRI  KSFTDKMILP  RIKGKTVLNL  NHLLQYNPQQ  IDISNTRATQ  SQFEKWYEGV  RNDYGLNDNE  MQVMLNGLMV  WCIENGTSPD
BrazilcpP    GERDRDVNVG  TSGTFTVPRT  KSFTDKMILP  RIKGKTVLNL  NHLIQYNPQQ  IDISNTRATQ  SQFEKWYEGV  RNDYGLNDNE  MQIVLNGLMV  WCIENGTSPD
```

FIG. 9B

```
              301
Fla831cpW     ISGVWVMMDD TTGTQVDYPI KPLIEHATPS FRQIMAHFSN AAEAYIARRN ATERYMPRYG IKRNLTDISL ARYAFDFYEV NSKTPDRARE ARMQMKAAAL
HacpP         ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
UsacpP        ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
UsacpW        ISGVWVMMDG ..ETQVDYPI KPLIEHATPS FRQIMAHFSN AAEAYIAKRN ATERYMPRYG IKRNLTDISL ARYAFDFYEV NSKTPDRARE AHMQMKAAAL
YkcpP         ISGVWVMMDG ..ETQVDYPI KPLIEHATPS FRQIMAHFSN AAEAYIAKRN ATEKYMPRYG IKRNLTDISL ARYAFDFYEV NSKTPDRARE AHMQMKAAAL
AustraliancpW ISGVWVMMDG ..ETQVDYPI KPLIEHATPT FRQIMAHFSN AAEAYIAKRN ATERYMPRYG IKRNLTDISL ARYAFDFYEV NSKTPDRARE AHMQMKAAAL
BrazilcpP     ISGVWVMMDG ..ETQVDYPI KPLIEHATPS FRQIMAHFSN AAEAYITKRN ATERYMPRYG IKRNLTDISL ARYAFDFYEV NSKTPDRARE AHMQMKAAAL
                                                                                                                    400

401
Fla831cpW     RNTNRRMFGM DGSVSNKEEN TERHTVEDVN RDMHSLLGMR N*
HacpP         RNTSRRMFGM DGSVSNKEEN TERHTVEDVN RDMHSLLGMR N*
UsacpP        RNTSRKMFGM DGSVSNKEEN TERHTVEDVN RDMHSLLGMR N*
UsacpW        RNTSRRMFGM DGSVSNKEEN TERHTVEDVN RDMHSLLGMR N*
YkcpP         RNTNRKMFGM DGSVSNKEEN TERHTVEDVN RDMHSLLGMR N*
AustraliancpW RNTSRRMFGM DGSVSNKEEN MERHTVEDVN RDMHSLLGMR N*
BrazilcpP     RNTNRRMFGM DGSVSNKEEN TERHTVEDVN RDMHSLLGMR N*
                                                      500
```

COAT PROTEIN GENE FOR THE FLA83 W STRAIN OF PAPAYA RINGSPOT VIRUS

This application is a 371 of PCT/US95/07272, filed on Jun. 7, 1995, which is a continuation-in-part of U.S. Ser. No. 08/366,881, filed on Dec. 30, 1994, now abandoned.

FIELD OF THE INVENTION

This invention relates to a coat protein gene derived from papaya ringspot virus. More specifically, the invention relates to the genetic engineering of plants and to a method for conferring viral resistance to a plant using an expression cassette encoding papaya ringspot virus PRV FLA83 W coat protein.

BACKGROUND OF THE INVENTION

Many agriculturally important crops are susceptible to infection by plant viruses, particularly papaya ringspot virus, which can seriously damage a crop, reduce its economic value to the grower, and increase its cost to the consumer. Attempts to control or prevent infection of a crop by a plant virus such as papaya ringspot virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Potyviruses are a distinct group of plant viruses which are pathogenic to various crops, and which demonstrate cross-infectivity between plant members of different families. Generally, a potyvirus is a single-stranded RNA virus that is surrounded by a repeating protein monomer, which is termed the coat protein (CP). The majority of the potyviruses are transmitted in a nonpersistent manner by aphids. As can be seen from the wide range of crops affected by potyviruses, the host range includes such diverse families of plants as Solanaceae, Chenopodiaceae, Gramineae, Compositae, Leguminosae, Dioscroeaceae, Cucurbitaceae, and Caricaceae. Potyviruses include watermelon mosaic virus II (WMVII); zucchini yellow mosaic virus (ZYMV), potato virus Y, tobacco etch and many others.

Another potyvirus of economic significance is papaya ringspot virus (PRV). Two groups of PRV have been identified: the "P" or "papaya ringsEpot" type infects papayas; and the "W" or "watermelon" type infects cucurbits, e.g., squash, but it is unable to infect papaya. Thus, these two groups can be distinguished by host range differences.

The potyviruses consist of flexous, filamentous particles of dimensions approximately 780×12 nanometers. The viral particles contain a single-stranded positive polarity RNA genome containing about 10,000 nucleotides. Translation of the RNA genome of potyviruses shows that the RNA encodes a single large polyprotein of about 330 kD. This polyprotein contains several proteins; these include the coat protein, nuclear inclusion proteins NIa and NIb, cytoplasmic inclusion protein (CI), and other proteases and movement proteins. These proteins are found in the infected plant cell and form the necessary components for viral replication. One of the proteins contained in the polyprotein is a 35 kD capsid or coat protein which coats and protects the viral RNA from degradation. One of the nuclear inclusion proteins, NIb, is an RNA replicase component and is thought to have polymerase activity. CI, a second inclusion protein, is believed to participate in the replicase complex and have a helicase activity. NIa, a third inclusion protein, has a protease activity. In the course of potyvirus infection, NIa and NIb are translationally transported across the nuclear membrane into the nucleus of the infected plant cell at the later stages of infection and accumulate to high levels.

The location of the protease gene appears to be conserved in these viruses. In the tobacco etch virus, the protease cleavage site has been determined to be the dipeptide Gln-Ser, Gln-Gly, or Gln-Ala.

Conservation of these dipeptides at the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. For reviews, see Fitchen et al., *Annu. Rev. Microbiol.,* 47, 739 (1993) and Wilson, *Proc. Natl. Acad. Sci. USA,* 90, 3134 (1993). For papaya ringspot virus, Ling et al. (*Bio/Technology,* 9, 752 (1991)) found that transgenic tobacco plants expressing the PRV coat protein gene isolated from the PRV strain HA 5-1 (mild) showed delayed symptom development and attenuation of symptoms after infection by a number of potyviruses, including tobacco etch (TEV), potato virus Y (PVY), and pepper mottle virus (PeMV). PRV does not infect tobacco, however. Thus, PRV CP transgenic tobacco plants cannot be used to evaluate protection against PRV. Fitch et al. (*Bio/Technology,* 10, 1466 (1992)), Gonsalves (*American J. of Bot.,* 79, 88 (1992)), and Lius et al., 91*st Annual Meeting of the American Society for Horticultural Science Hortscience,* 29, 483 (1994)) reported that four $R_0$ papaya plants made transgenic for a PRV coat protein gene taken from strain HA 5-1 (mild) displayed varying degrees of resistance against PRV infection, and one line (S55-1) appeared completely resistant to PRV. This appears to be the only papaya line that shows complete resistance to PRV infection.

Thus, there is a continuing need for the transgenic expression of genes derived from potyviruses at levels which confer resistance to infection by these viruses.

SUMMARY OF THE INVENTION

This invention provides an isolated and purified DNA molecule that encodes the coat protein for the FLA83 W-type strain of papaya ringspot virus (PRV). The invention also provides a chimeric expression cassette comprising this DNA molecule, a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed mRNA sequences, wherein the promoter is operably linked to the DNA molecule, and the DNA molecule is operably linked to the polyadenylation signal. Another embodiment of the invention is exemplified by the insertion of multiple virus gene expression cassettes into one purified DNA molecule, e.g., a plasmid. Preferably, these cassettes include the promoter of the 35S gene of cauliflower mosaic virus and the polyadenylation signal of the cauliflower mosaic virus 35S gene.

Also provided are bacterial cells, and transformed plant cells, containing the chimeric expression cassettes comprising the coat protein gene derived from the FLA83 W-type strain of papaya ringspot virus (referred to herein as PRV FLA83 W), and preferably the 35S promoter of cauliflower mosaic virus and the polyadenylation signal of the cauliflower mosaic virus 35S gene. Plants are also provided, wherein the plants comprise a plurality of transformed cells transformed with a cassette containing the coat protein gene derived from the PRV FLA83 W strain, and preferably the cauliflower mosaic virus 35S promoter and the polyadenylation signal of the cauliflower mosaic virus gene. Transformed plants of this invention include tobacco, corn, cucumber, peppers, potatoes, soybean, squash, and tomatoes. Especially preferred are members of the Cucurbitaceae (e.g., squash and cucumber) family.

Another aspect of the present invention is a method of preparing a PRV-resistant plant, such as a dicot, comprising: transforming plant cells with a chimeric expression cassette comprising a promoter functional in plant cells operably linked to a DNA molecule that encodes a coat protein as described above; regenerating the plant cells to provide a differentiated plant; and identifying a transformed plant that expresses the PRV coat protein at a level sufficient to render the plant resistant to infection by the specific strains of PRV disclosed herein.

As used herein, with respect to a DNA molecule or "gene," the phrase "isolated and purified" is defined to mean that the molecule is either extracted from its context in the viral genome by chemical means and purified and/or modified to the extent that it can be introduced into the present vectors in the appropriate orientation, i.e., sense or antisense. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, the term "expression" is defined to mean transcription or transcription followed by translation of a particular DNA molecule.

BRIEF DESCRIPTION OF THE DRAWINGS

FIGS. 1A–1B. The nucleotide sequence of the coat protein gene (long version) of PRV FLA83 W [SEQ ID NO:1]. The amino acid sequence of the encoded open reading frame is shown below the nucleotide sequence [SEQ ID NOS:2and 3].

FIGS. 2A–2B. The nucleotide sequence of the coat protein gene (short version) of PRV FLA83 W [SEQ ID NO:4]. The amino acid sequence of the encoded open reading frame is shown below the nucleotide sequence [SEQ ID NOS:5and 6 ].

FIGS. 3A–3C. The alignment of the nucleotide sequences of the PRV FLA83 W long (LG) and short (SH) coat protein genes [SEQ ID NOS:1 and 4]. The primer pairs RMM384-385 and RMM388-385 are shown [SEQ ID NOS:7, 8, and 9]. The primer pairs RMM384-385 and RMM388-385 were used to PCR amplify and install novel NcoI restriction sites for LG and SH coat protein genes, respectively. The viral-specific sequences present in RMM384, RMM385, and RMM388 are homologous to sequences in PRV HA (attenuated) USA P (Quemada et al., *J. Gen. Virol.,* 71, 203 (1990)). In addition, all three oligomers contain novel NcoI sites (underlined sequences).

FIGS. 4A–4C. The alignment of the coat protein coding sequences from papaya ringspot virus isolates: Australian W (Bateson et al., *Arch-Viol,* 123, 101 (1992)) [SEQ ID NO:10]; HA P (Yeh et al., *J. Gen. Virol.,* 73:2531 (1992)) [SEQ ID NO:11]; USA P (Quemada et al., *J. Gen. Virol.,* 71, 203 (1990)) [SEQ ID NO:12]; USA-W (Quemada et al., *J. Gen. Virol.,* 71, 203 (1990)) [SEQ ID NO:13]; and FLA83 W SH [SEQ ID NO:4]. Alignments were generated using the UWGCG Pileup program. The dots represent either the lack of sequence information at the ends of the coat protein gene or gaps in homology in sequences relative to others in the alignment.

FIGS. 5A–5B. The alignment of the coat protein amino acid sequences from papaya ringspot virus isolates: Australian W [SEQ ID NO:14]; HA P [SEQ ID NO:15]; USA P [SEQ ID NO:16]; USA W [SEQ ID NO:17]; and FLA83 W LG and SH [SEQ ID NOS:2, 3 and 5, 6]. Alignments were generated using the UWGCG Pileup program. The dots represent either the lack of sequence information at the 5' end of the coat protein gene or gaps in homology in sequences relative to others in the alignment. Sequence homology differences between virus strains are underlined. The deduced amino acid sequence of the PRV FLA83 W coat protein (CP) gene disclosed here is unique compared with the PRV coat protein amino acid sequences of the four strains shown in the figure. The PRV FLA83 CP amino acid sequence differs from all other published PRV CP sequences in at least 14 positions (Numbers 1–14). The FLA83 W CP gene possesses a 6-bp insertion (FIG. 4) relative to other PRV CP genes characterized to date (see "INSERTION" in FIG. 5). This 6-bp insertion codes for the amino acids threonine—threonine.

FIGS. 6A–6B. A schematic diagram of the cloning strategy for the long version of PRV coat protein gene (PRVFLA83cp16[s] and [as]). Single stranded cDNA was produced with PRV virion RNA as template and reverse transcriptase. After PCR amplification, the PCR product was digested with NcoI and inserted into the NcoI site of pUC18cpexpress to yield sense and antisense constructs.

FIGS. 7A–7B. A schematic representation of the cloning strategy for the short version of PRV coat protein (PRVFLA83cp34 [s] and [as]). Single stranded cDNA was produced with PRV virion RNA as template and reverse transcriptase. After PCR amplification, the PCR product was digested with NcoI and inserted into the NcoI site of pUC18cpexpress to yield sense and antisense constructs.

FIGS. 8A–8C. The alignment of nucleotide sequences for seven isolates (Fla831cpW, HacpP, UsacpP, UsacpW, AustraliancpW, BrazilcpP (SEQ ID NO: 10) and YkcpP (SEQ ID NO: 19)) of PRV.

FIGS. 9A–9B. The alignment of amino acid sequences for seven isolates (Fla831cpW, HacpP, UsacpP, UsacpW, AustraliancpW, BrazilcpP (SEQ ID NO:20) and YkcpP (SEQ ID NO: 21)) of PRV.

FIG. 10. The theoretical relations between the seven PRV isolates of FIGS. 8 and 9.

DETAILED DESCRIPTION OF THE INVENTION

Papaya Ringspot Virus (PRV) is a single-stranded (+) RNA plant virus. The viral genome is approximately 10,000 bases in length. The expression strategy of potyviruses includes translation of a complete polyprotein from the positive sense viral genomic RNA. Translation of the genomic RNA produces a 330 kD protein which is subsequently cleaved into at least seven smaller viral proteins by a virally encoded protease. The virally encoded proteins include a 35 kD protein at the amino terminal end of the 330 kD protein which is thought to be involved in cell to cell transmission, H C protein is 56 kD in size and is believed to be involved in insect transmission and possess proteolytic activity, a 50 kD protein, a 90 kD cylindrical inclusion protein (CI) which is part of the replicase complex and possesses helicase activity, a 6 kD VPg protein which is covalently attached to the 5' end of the viral genomic RNA, a 49 kD NIa protein which functions as a protease, a 60 kD NIb protein which functions as a polymerase, and the coat protein (36 kD).

Two types of PRV have been established based on host range. One type is designated "P type"; it infects Caricacae (e.g., papaya), Cucurbitaceae (e.g., cucurbitis), and Chenopodiaceae (e.g., Chenopodium) (Wang et al., *Phytopathology*, 84, 1205 (1994)). A second type is designated "W.type"; it infects only Cucurbitaceae and Chenopodiaceae (Wang et al., *Phytopathology*, 84, 1205 (1994)). Isolates of the P type include HA-severe (Wang et al., *Virus Arch. Virol.*, 127, 345 (1992)), HA5-1, called USA P herein, YK (Wang et al., *Phytopathology*, 84, 1205 (1994)), and other isolates as described in Tennant et al. (*Phytopathology*, 84, 1359 (1994)). Isolates of the W type include FLA83, disclosed herein, PRV-W type (Yeh et al., *Phytopath.*, 74, 1081 (1984)) and PRV-W (Aust) (Bateson et al., *Arch-Viol*, 123, 101 (1992)).

Previous work has shown that the potyvirus NIa protease cleaves the coat protein from the adjacent protein NIb (Restrepo-Hartwig et al., *J. Virol.*, 66, 5662 (1992); Dougherty et al., *Ann. Rev. Phytopath.*, 26, 123 (1988); Carrington et al., *J. Virol.*, 61, 2540 (1987)). The determination of the N-terminal amino acid sequences of the coat protein have been problematic (Yeh et al., *J. Gen. Virol.*, 73, 2531 (1992); Wang et al., *Virus Arch. Virol.*, 127, 345 (1992)), therefore the amino terminus of the coat protein remains unclear. The sites predicted for the NIa/coat protein cleavage site are underlined in FIG. 5 (VFHQ/SKNE in Quemada et al., *J. Gen. Virol*, 71, 203 (1990); VFHQ/SKNE in Bateson et al., *Arch. Viol.*, 123, 101 (1992); VYHE/SRGTD in Yeh et al., *J. Gen. Virol.*, 73, 2531 (1992); VLEQ/APFN and VFHQ/AKNE described herein).

To practice the present invention, the coat protein gene of a virus must be isolated from the viral genome and inserted into a vector. Thus, the present invention provides isolated and purified DNA molecules that encode the coat protein of PRV FLA83. As used herein, a DNA molecule that encodes a coat protein gene includes nucleotides of the coding strand, also referred to as the "sense" strand, as well as nucleotides of the noncoding strand, complementary strand, also referred to as the "antisense" strand, either alone or in their base-paired configuration. Thus, a DNA molecule that encodes the coat protein of PRV FLA83, for example, includes the DNA molecule having the nucleotide sequence of FIG. 1 [SEQ ID NO:1], a DNA molecule complementary to the nucleotide sequence of FIG. 1 [SEQ ID NO:1], as well as a DNA molecule which also encodes a PRV coat protein and its complement which hybridizes with a PRV FLA83-specific DNA probe in hybridization buffer with 6XSSC, 5X Denhardt's reagent, 0.50% SDS and 100 μg/mL denatured, fragmented salmon sperm DNA and remains bound when washed at 68° C. in 0.1XSSC and 0.5% SDS (Sambrook et al., *Molecular Cloning: A Laboratory Manual*, 2nd ed. (1989)). Moreover, the DNA molecules of the present invention can include non-PRV coat protein nucleotides that do not interfere with expression. Preferably, the isolated and purified DNA molecules of the present invention comprise a single coding region for the coat protein. Thus, preferably the DNA molecules of the present invention are those "consisting essentially of" DNA that encodes the coat protein.

The PRV coat protein gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate a viral gene. To do so, one having ordinary skill in the art can use information about the genomic organization of potyviruses to locate and isolate the coat protein gene. The coat protein gene is located at the 3' end of the RNA, just prior to a stretch of about 200–300 adenine nucleotide residues. Additionally, the information related to proteolytic cleavage sites is used to determine the N-terminus of the potyvirus coat protein gene. The protease recognition sites are conserved in the potyviruses and have been determined to be either the dipeptide Gln-Ser, Gln-Gly, or Gln-Ala. The nucleotide sequences which encode these dipeptides can be determined.

Using methods well known in the art, a quantity of virus is grown and harvested. The viral RNA is then separated and a viral gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the coat protein. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

Previously isolated PRV coat protein genes can be used as hybridization probes to screen the cDNA library to determine if any of the transformed bacteria contain DNA fragments with sequences coding for the PRV coat protein region. The cDNA inserts in any bacterial colonies which contain this region can be sequenced. The coat protein gene is present in its entirety in colonies which have sequences that extend 5' to a sequence which encodes a N-terminal proteolytic cleavage site and 3' to a stop codon.

Alternatively, cDNA fragments can be inserted in the sense orientation into expression vectors. Antibodies against the coat protein can be used to screen the cDNA expression library and the gene can be isolated from colonies which express the protein.

Another molecular strategy to provide virus resistance in transgenic plants is based on antisense RNA. As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited in the cell by the presense of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature,* 333:866–869 (1988)); or at a more subtle biochemical level, e.g., change in the amount of polygalacturonase and reduction in depolymerization of pectin during tomato fruit ripening (Smith et al., *Nature,* 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology," Abstract X1-022 (1994)). Thus, both antisense and sense RNA have been proven to be useful in achieving downregulation of gene expression in plants.

In the present invention, the DNA molecule encoding the coat protein gene of the papaya ringspot virus strain FLA83 has been determined and the gene has been inserted into an expression vector. These expression cassettes can be individually placed into a vector that can be transmitted into plants, preferably a binary vector. Alternatively, two or more PRV coat protein genes can each be present in an expression cassette which can be placed into the same binary vector, or a PRV coat protein expression cassette of the present invention can be placed into a binary vector with one or more viral gene expression cassettes. The expression vectors contain the necessary genetic regulatory sequences for expression of an inserted gene. The coat protein gene is inserted such that those regulatory sequences are functional and the genes can be expressed when incorporated into a plant genome. For example, vectors of the present invention can contain combinations of expression cassettes that include DNA from PRVcoat protein genes other than those of FLA83 (i.e., heterologous PRV coat protein genes), a cucumber mosaic virus coat protein gene, a squash mosaic virus coat protein gene, a zucchini yellow mosaic virus coat protein gene, and a watermelon mosaic virus-2 coat protein gene.

Moreover, when combinations of viral gene expression cassettes are placed in the same binary plasmid, and that multigene cassette containing plasmid transformed into a plant, the viral genes all preferably exhibit substantially the same degrees of efficacy when present in transgenic plants. For example, if one examines numerous transgenic lines containing two different intact viral gene cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the efficacy of each gene in these multiple gene constructs, this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' Assignees copending patent application Ser. No. 08/366,991 entitled "Transgenic Plants Expressing DNA Constructs Containing a Plurality of Genes to Impart Virus Resistance" filed on Dec. 30, 1994, and incorporated by reference herein.

In order to express the viral gene, the necessary genetic regulatory sequences must be provided. Since the coat protein of a potyvirus is produced by the post-translational processing of a polyprotein, the coat protein gene isolated from viral RNA does not contain transcription and translation signals necessary for its expression once transferred and integrated into a plant genome. It must, therefore, be engineered to contain a plant expressible promoter, a translation initiation codon (ATG), and a plant functional poly(A) addition signal (AATAAA) 3' of its translation termination codon. In the present invention, the coat proteins are inserted into vectors which contain cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plants or plant viruses, and can include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present viral gene expression cassettes include the constitutive promoters from CaMV, the Ti genes nopaline synthase (Bevan et al., *Nucleic*

*Acids Res. II,* 369 (1983)) and octopine synthase (Depicker et al., *J. Mol. Appl. Genet.,* 1, 561 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity to accomplish the expression of the preselected proteins and subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' nontranslated region which is employed is one which will cause the termination of transcription and the addition of polyadenylated ribonucleotides to the 3' end of the transcribed mRNA sequence. The termination region can be native with the promoter region, native with the gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of Agrobacterium tumor-inducing (Ti) plasmid genes, such as the nopaline synthase (NOS) gene; and (2) plant genes like the soybean 7S storage protein genes.

Preferably, the expression cassettes: of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from cauliflower mosaic virus (CaMV). The poly(A) signal can be obtained from the CaMV 35S gene or from any number of well characterized plant genes, i.e., nopaline synthase, octopine synthase, and the bean storage protein gene phaseolin. The constructions are similar to that used for the expression of the CMV C coat protein in PCT Patent Application PCT/US88/04321, published on Jun. 29, 1989 as WO 89/05858, claiming the benefit of U.S. Ser. No. 135,591, filed Dec. 21, 1987, entitled "Cucumber Mosaic Virus Coat Protein Gene," and the CMV WL coat protein in PCT Patent Application PCT/US89/03288, published on Mar. 8, 1990 as WO 90/02185, claiming the benefit of U.S. Ser. No. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species, one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as *E. coli*. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in *E. coli* cells.

All DNA manipulations are typically carried out in *E. coli* cells, and the final plasmid bearing the potyvirus gene expression cassette is moved into Agrobacterium cells by direct DNA transformation, conjugation, and the like. These Agrobacterium cells will contain a second plasmid, also derived from Ti or Ri plasmids. This second plasmid will carry all the viral genes required for transfer of the foreign DNA into plant cells. Suitable plant transformation cloning vectors include those derived from a Ti plasmid of *Agrobacterium tumefaciens,* as generally disclosed in Glassman et al. (U.S. Pat. No. 5,258,300), or *Agrobacterium rhizogenes.*

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, transformation using viruses or pollen, chemicals that increase the direct uptake of DNA (Paszkowski et al., *EMBO J.,* 3, 2717 (1984)), microinjection (Crossway et al., *Mol. Gen. Genet.,* 202, 179 (1985)), electroporation (Fromm et al., *Proc. Natl. Acad. Sci. USA,* 82, 5824 (1985)), or high-velocity microprojectiles (Klein et al., *Nature,* 327, 70 (1987)).

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present potyvirus multi-gene expression cassette for an effective period of time. This can range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or callus can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in a root-inducing compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcript-Lon of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity to that of the viral genomic RNA such that they are capable of base pairing with viral genomic RNA under conditions described in Chapter 7 in Sambrook et al. (1989).

The presence of a viral coat protein gene can also be detected by immunological assays, such as the double-antibody sandwich assays described by Namba et al., *Gene,* 107, 181 (1991) as modified by Clark et al., *J.*

Gen. Virol., 34, 475 (1979). See also, Namba et al., *Phytopathology,* 82, 940 (1992). Potyvirus resistance can also be assayed via infectivity studies as generally disclosed by Namba et al., *ibid.,* wherein plants are scored as symptomatic when any inoculated leaf shows veinclearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to convert agronomically elite, yet sensitive lines to resistant lines. A conversion process (backcrossing) is carried out by crossing the original transgenic resistant line with a sensitive elite line and crossing the progeny back to the sensitive parent. The progeny from this cross will segregate such that some plants carry the resistance gene(s) whereas some do not.

Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples. Enzymes were obtained from commercial sources and were used according to the vendor's recommendations or other variations known in the art. Other reagents, buffers, etc., were obtained from commercial sources, such as GIBCO-BRL, Bethesda, Md., and Sigma Chemical Co., St. Louis, Mo., unless otherwise specified.

Figure 6B:
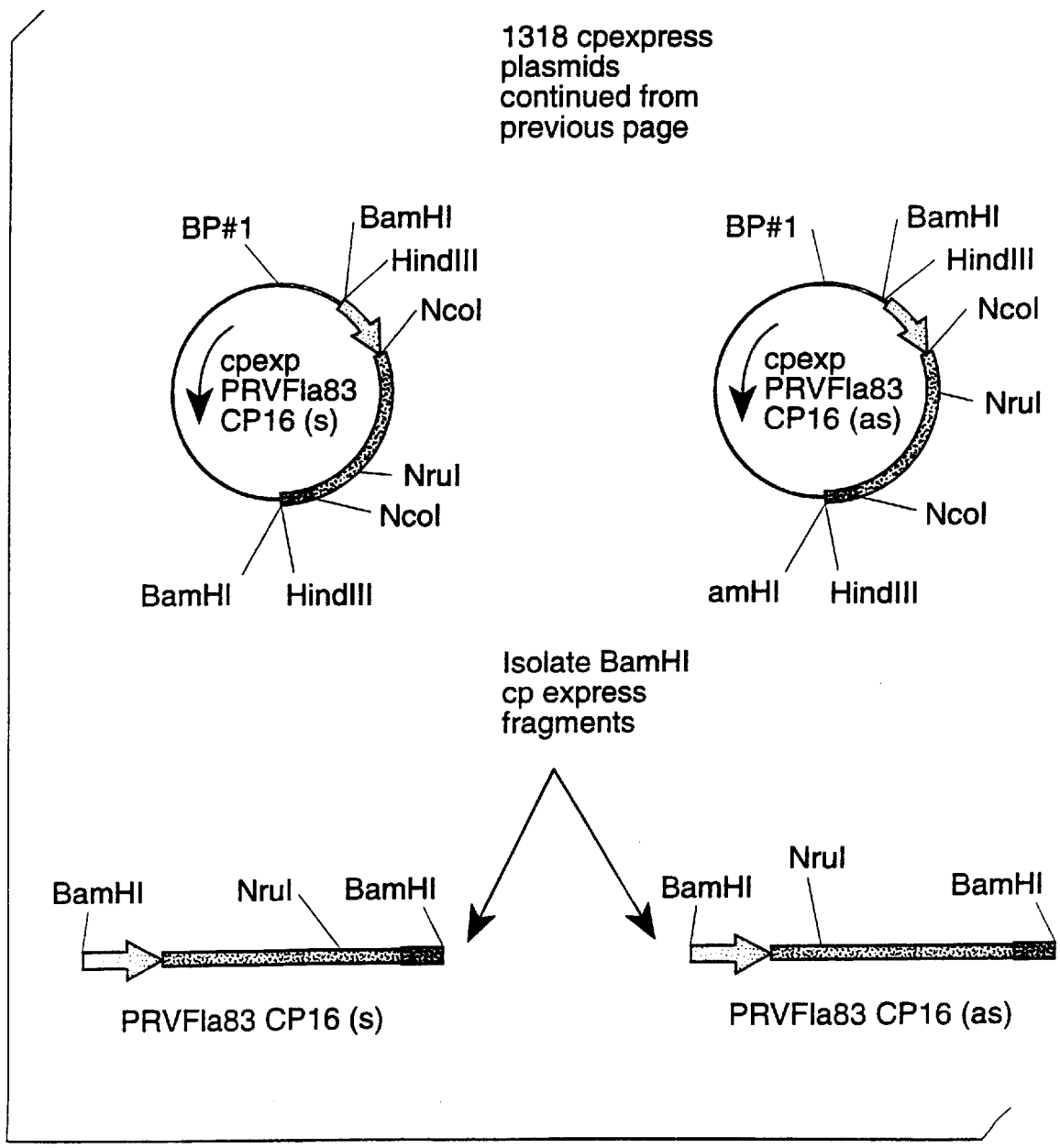
Figure 7A:
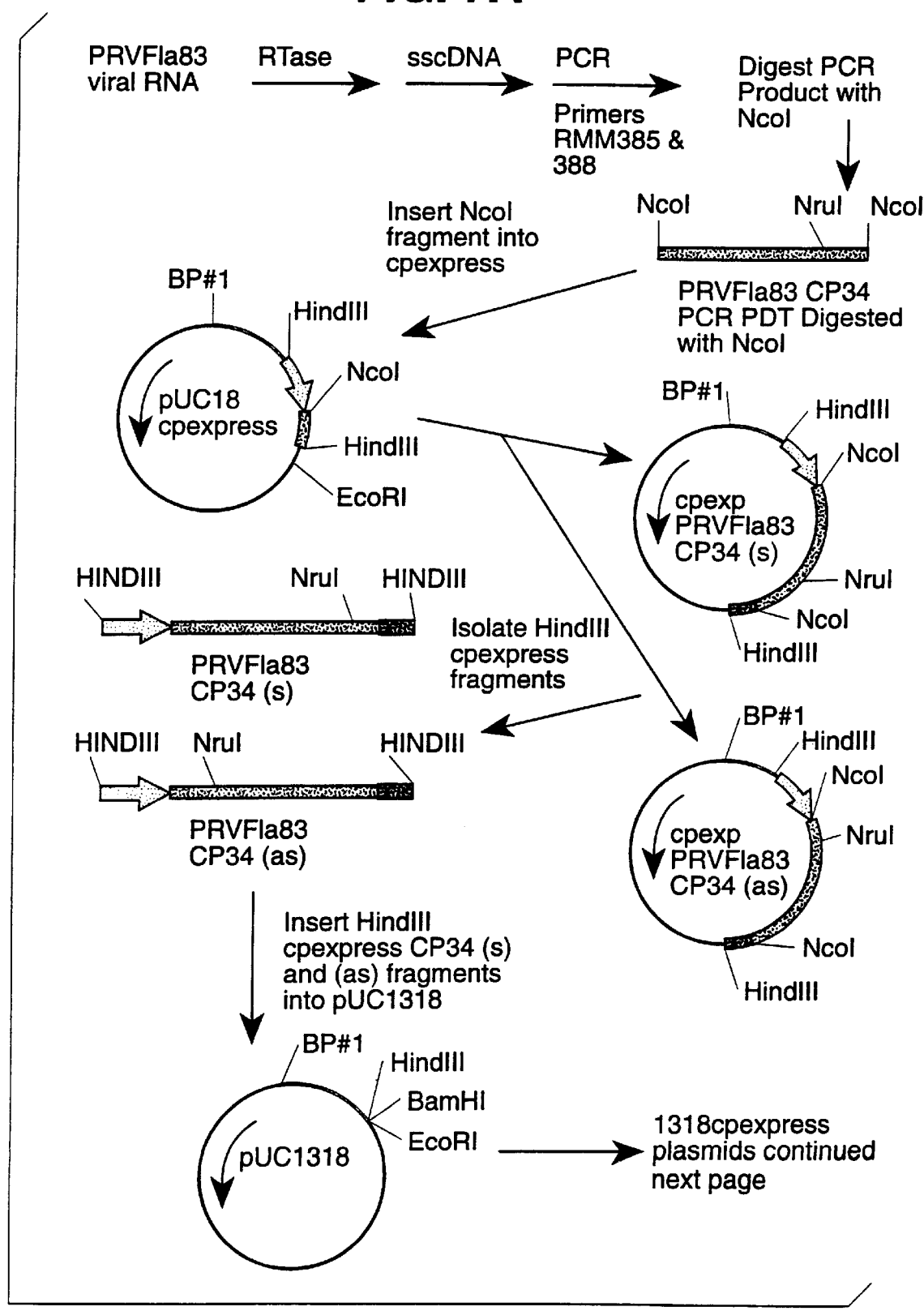
Figure 7B:
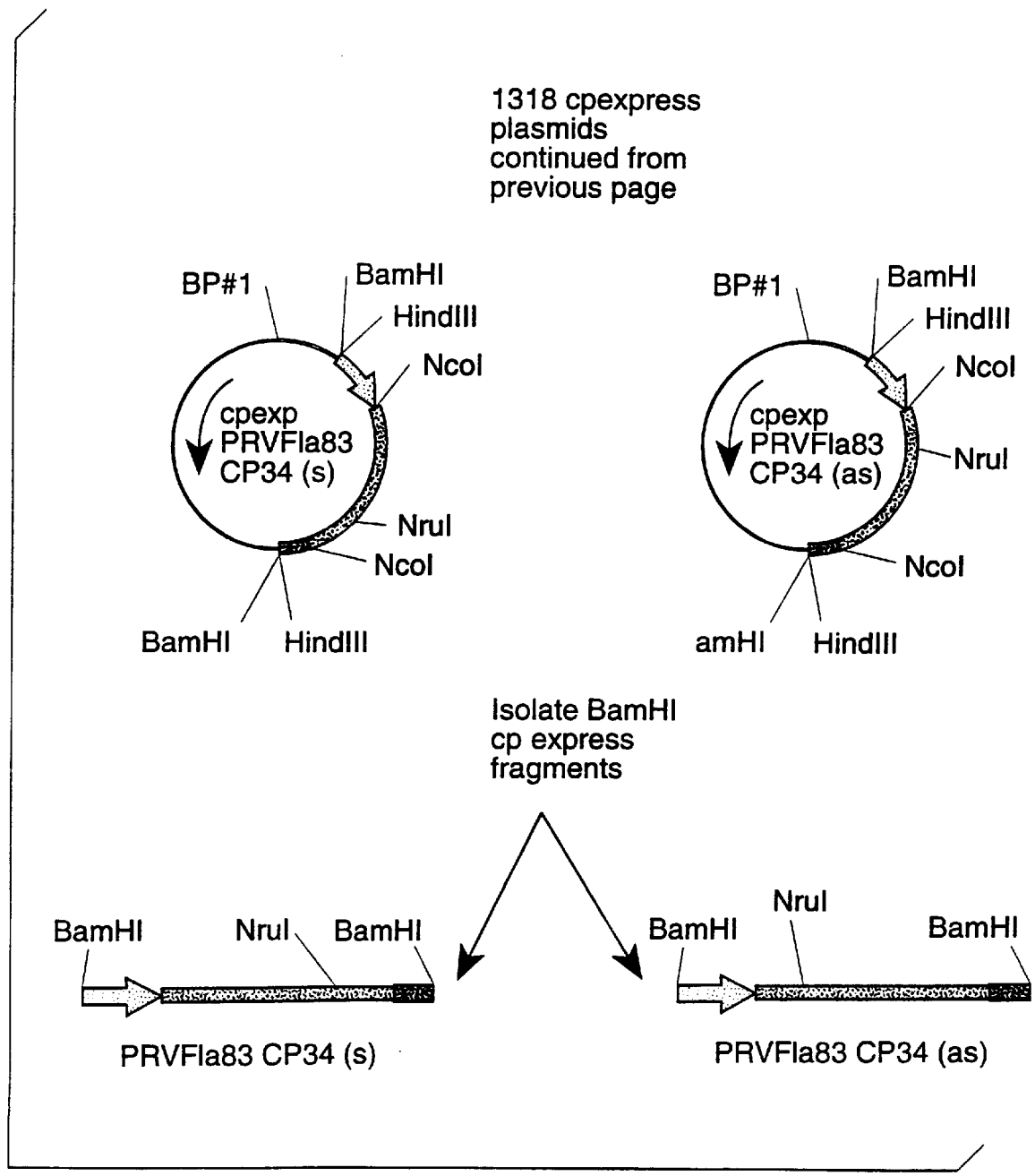
Figure 10:
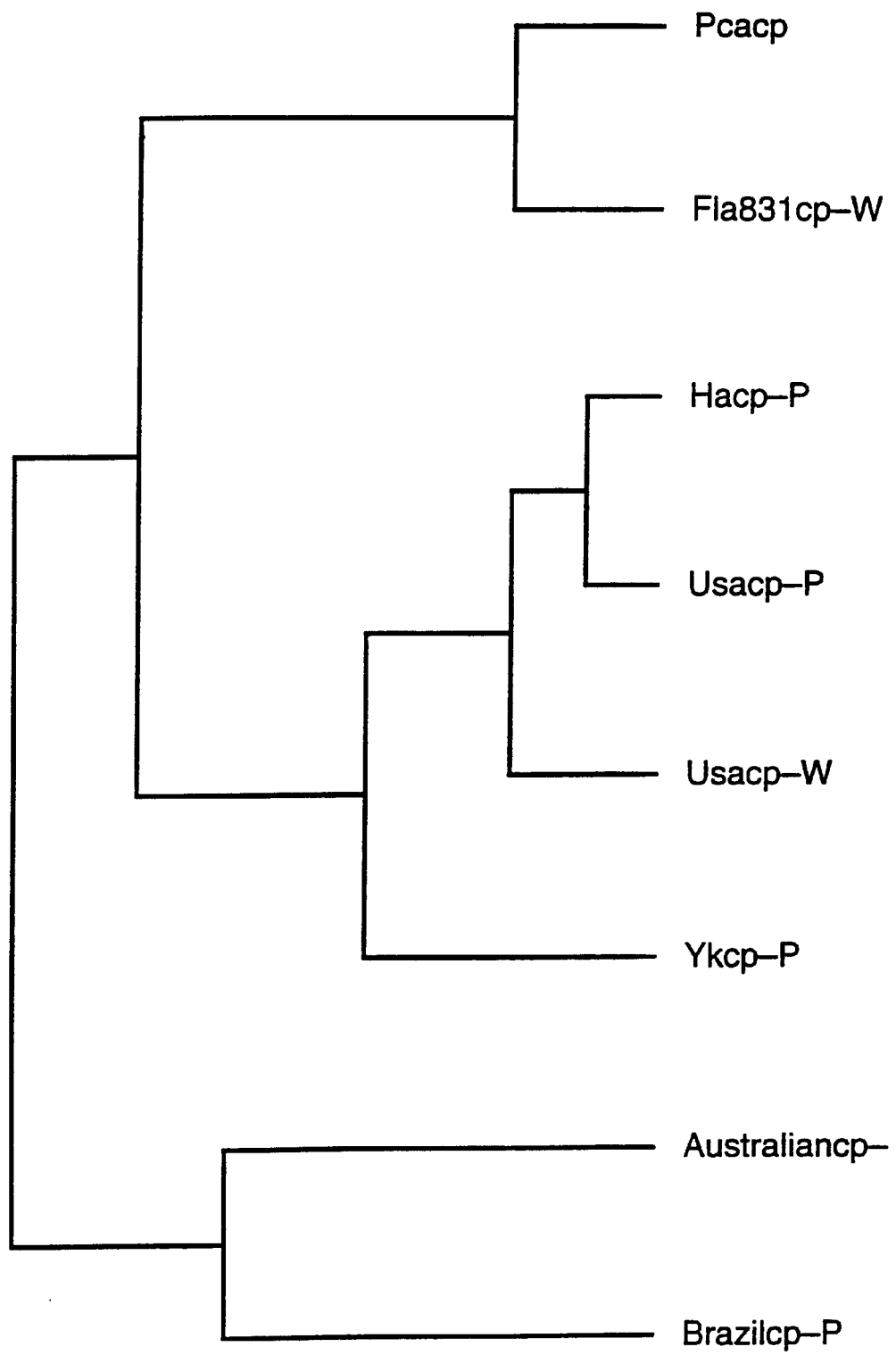

Most of the recombinant DNA methods employed in practicing the present invention are standard procedures, well known to those skilled in the art, and described in detail in, for example, in European Patent Application Publication Number 223,452, published Nov. 29, 1986, which is incorporated herein by reference. General references containing such standard techniques include the following: R. Wu, ed., *Methods in Enzymology, Vol.* 68 (1979); J. H. Miller, *Experiments in Molecular Genetics* (1972); J. Sambrook et al., *Molecular Cloning: A Laboratory Manual,* 2nd ed. (1989); and D. M. Glover, ed., *DNA Cloning Vol. II* (1982). FIGS. 6 and 7 are presented to illustrate constructions of this invention.

Papaya Ringspot virus FLA83W -type was deposited with the American Type Culture Collection (ATCC), 10801 University Blvd., Manassas, Va. on Aug. 3, 1998 and assigned ATCC Deposit Number 203076. This deposit was made in compliance with the requirements of the Budapest Treaty that the duration of this deposit should be for thirty (30) years from the date of deposit or for five (5) years after the last request for the deposit at the depository or for the enforceable life of a U.S. Patent that matures from this application, whichever is longer. Plant virus strain of FLA 83W -type will be replenished should this virus become non-viable at the depository.

Example I
A. Isolation of FLA83 W RNAs

Crookneck squash plants (7-days old) were inoculated with PRV strain W (watermelon) Florida-83; after 21 days, infected leaves were harvested and PRV virus particles were isolated. The procedure used was based on protocols from Purcifull et al. (*Phytopathology,* 69, 112 (1979)) for PRV type W isolation. Approximately 50 g of fresh leaf tissue were extracted in 100 mL of 0.5 M potassium phosphate buffer (pH 7.5, "PB") containing 0.1% sodium sulfate, 25 mL of chloroform, and 25 mL of carbon tetrachloride. After centrifugation of the extract at 1000× g for 5 minutes, the pellet was resuspended in 50 mL of PB buffer and centrifuged again at 1000× g for 5 minutes. The supernatants from each centrifugation were pooled, then centrifuged at 13,000× g for 15 minutes. To the supernatant was added TRITON X-100 to a final concentration of 1% (v/v), polyethylene glycol (PEG) 8,000 (Research Grade from Sigma Chemical Co.) to a final concentration of 4%, (w/v) and NaCl to a final concentration of 100 mM. The suspension was stirred for 1 hour at 0–4° C. It was then centrifuged at 10,000× g for 10 minutes.

The virus pellet was collected and resuspended in about 40 mL of PB buffer. After centrifugation at 12,000× g for 10 minutes, the pellet was discarded and virus was precipitated by adding PEG to a final concentration of 8% (w/v) and NaCl to a final concentration of 100 mM and stirring for 0.5 hour at 0–4° C. After centrifugation at 12,000× g for 10 minutes the pellets were resuspended with the aid of a tissue grinder in 5 mL of 20 mM PB buffer and layered over a 30% $Cs_2SO_4$ cushion. This was centrifuged in a Beckman Ti75 at 140,000× g for 18 hours at 5° C. After centrifugation, the virus band was harvested, and dialyzed against 20 mM PB buffer overnight at 4° C. The dialyzed virus preparation was lysed and viral RNA precipitated with LiCl (2 M final concentration). The viral RNA was recovered by centrifugation. Viral RNA was dissolved and precipitated by ethanol and resuspended in water.

B. Cloning and Engineering PRV FLA83 Coat Protein Gene

To obtain engineered genes of the PRV strain FLA83 coat protein gene, the following steps were carried out: 1) single-stranded cDNA of PRV FLA83 was constructed; 2) coat protein sequences were amplified by PCR; 3) the PRV CP PCR product was cloned; 4) expression cassettes were inserted into binary vectors; 5) plants transgenic for the PRV CP construct were produced; and 6) progeny of $R_0$ transgenic plants were challenged to identify protected lines.

Single-stranded cDNA of PRV FLA83 W RNA was synthesized with the use of ClonStruct™ cDNA Library Construction Kit reagents (US Biochemical, Cleveland, Ohio). Briefly, a first strand cDNA synthesis reaction was primed with the vector primer pTRXN PLUS (US Biochemical, Cleveland, Ohio). This vector includes a poly dT tract; the plasmid poly dT tract anneals with the poly $A^+$ tail of PRV RNA. Subsequently, the PRV first strand cDNA was synthesized; the reaction extended the pTRXN plasmid primer.

PRV single-stranded CDNA was used as a template to PCR amplify PRV coat protein sequences. Two versions of the coat protein coding sequence were amplified: long (primers used were RMM384 and RMM385) and a short version (primers used were RMM388 and RMM385) (FIG. 3 [SEQ ID NOS:7, 8 and 9 for RMM384, RMM385, and RMM 388, respectively]). Sequences for NcoI sites were included in each of these primers, so that the PCR products contained NcoI sites which were generated during the amplification. After amplification, coat protein gene PCR products were digested with NcoI in preparation for insertion into the NcoI site of pUC18cpexpress. Both the long and short versions were installed into pUC18cpexpress. The long PRV FLA83 CP gene in cpexpress is known as FLA83CPpUC18cpexp16 (FIG. 6); the short PRV FLA83 CP gene in cpexpress is known as FLA83CPpUC18cpexp34 (FIG. 7).

The CP coding sequences of each were then nucleotide sequenced with the use of USB Sequenase Version II sequencing Kit (FIGS. 1 and 2 [SEQ ID NOS:1 and 4]). The coat protein gene sequence of the FLA83 PRV strain is novel information. Comparison with the coat protein genes of 5 different PRV strains shows that the CP gene of FLA83 differs from characterized coat protein sequences of other PRV strains in at: least 15 amino acid positions (FIG. 5).

After insertion into the expression cassette pUC18cpexpress, both sense and antisense cassettes were obtained (FIGS. 6 and 7). Subsequently, HindIII fragments harboring FLA83CPpUC18cpexp16 sense or antisense and FLA83CPpUC18cpexp34 sense or antisense were isolated and installed into the plasmid pUC1318 (Kay et al., *Nuc. Acids Res.,* 15:2778 (1987)) to provide additional cloning sites for insertion into binary vectors. Both sense and antisense versions of the long and short PRV FLA83 cassettes were excised as BamHI fragments and installed into the BglII site of binary plasmids. FLA83 coat protein expression cassettes were inserted in combination with other coat protein cassettes in binary vectors as summarized below in Table 1:

TABLE 1

| Binary | Parental Plasmid | Site | FLA83 CP Used | pEPG# |
|---|---|---|---|---|
| pGA482G | pEPG192 (V27cp) | XbaI | Short pUC1318cpexp34 (s) | 194 |
| pGA482G | pEPG191 (V27cp) | XbaI | Long pUC1318cpexp16 (s) | 241 |
| pGA482G | pEPG198 (V33cp) | XbaI | Short pUC1318cpexp34 (s) | 242 |
| pGA482G | pEPG198 (V33cp) | XbaI | Long pUC1318cpexp16 (s) | 249 |
| pPRBN | pEPG111 (CZW) | BglII | Long pUC18cpexp16 (s) | 208 or |
| pPRBN | pEPG111 (CZW) | BglII | Long pUC18cpexp16 (as) | 207 |
| pPRBN | pEPG111 (CZW) | BglII | Short pUC18cpexp34 (s) | 209 |
| pPRBN | pEPG111 (CZW) | BglII | Short pUC18cpexp34 (as) | 210 |
| pPBRN | pEPG109 (Cw1ZW) | BglII | Long pUC18cpexp16 (s) | 212 or 253 |
| pPBRN | pEPG109 (Cw1ZW) | BglII | Long pUC18cpexp16 (as) | 211 |
| pPRBN | pEPG109 (Cw1ZW) | BglII | Short pUCC18cpexp34 (s) | 213 |
| pPRBN | pEPG109 (Cw1ZW) | BglII | Short pUC18cpexp34 (as) | 214 |
| pGA482G | pEPG189 (CMV-C) | BglII | Long pUC18cpexp16 (s) | 216 |
| pGA482G | pEPG189 (CMV-C) | BglII | Long pUC18cpexp16 (as) | 215 |
| pGA482G | pEPB189 (CMV-C) | BglII | Short pUC18cpexp34 (s) | 218 |
| pGA482G | pEPG189 (CMV-C) | BglII | Short pUC18cpexp34 (as) | 220 |
| pGA482G | pEPG120 (Cw162) | BglII | Short pUC18cpexp34 (s) | 222 |
| pGA482G | pEPG120 (Cw162) | BglII | Short pUC18cpexp34 (as) | 223 |
| pGA482G | pEPG120 (Cw162) | BglII | Long pUC18cpexp16 (s) | 236 |
| pPRBN | pEPG106 (ZW) | HindIII | Long pUC18cpexp16 (as) | 203 |
| pPRBN | pEPG106 (ZW) | HindIII | Long pUC18cpexp16 (s) | 204 |
| pPRBN | pEPG106 (ZW) | HindIII | Short pUC18cpexp34 (s) | 205 |
| pPRBN | pEPG106 (ZW) | HindIII | Short pUC18cpexp34 (as) | 206 |
| pGA482G | pEPG321 (SqBV) | HpaI | Short pUC18cpexp34 (s) | 327* |
| pGA482G | pEPG321 (SqBV) | HpaI | Long pUC18cpexp16 (s) | 328# |

A BsrBI fragment, including all of the CP cassettes found in pEPG212, was isolated from pEPG212 and installed into the HpaI site of pEPG321 to give pEPG328.
*A BsrBI fragment, including all the CP cassettes found in pEPG213, was isolated from pEPG213 and installed into the HpaI site of pEPG321 to give pEPG327.

A BsrBI fragment, including all of the CP cassettes found in pEPG212, was isolated from pEPG212 and installed into the HpaI site of pEPG321 to give pEPG328.

*A BsrBI fragment, including all the CP cassettes found in pEPG213, was isolated from pEPG213 and installed into the HpaI site of pEPG321 to give pEPG327.

For further information on CMV-C and CMV-wl see Quemada et al., *J. Gen. Virol.*, 70, 1065 (1989). For further information on CMV V27 and V33 coat proteins, see Applicants' Assignees copending patent application Ser. No. 08/367,789 entitled "Plants Resistant to V27, V33, or V34 Strains of Cucumber Mosaic Virus" filed on Dec. 30, 1994, incorporated by reference herein. For further information on ZYMV and WMVII coat protein genes see Applicants' Assignees copending patent application Ser. No. 08/232,846 entitled "Potyvirus Coat Protein Genes and Plants Transformed Therewith" filed on Apr. 25, 1994, incorporated by reference herein. For further information on SqBV coat proteins see Applicants' Assignees copending patent application Ser. No. 08/085,250 entitled "Squash Mosaic Virus Genes and Plants Transformed Therewith" filed on Jun. 30, 1993, incorporated by reference herein.

Agrobacterium-mediated transfer of the plant expressible PRV coat protein genes described herein was done using the methods described in PCT published application WO 89/05859, entitled "Agrobacterium Mediated Transformation of Germinating Plant Seeds." Binary plasmids listed above (for further information, refer to Applicants' Assignees copending patent application Ser. No. 08/366,991 entitled "Transgenic Plants Expressing DNA Constructs Containing a Plurality of Genes to Impart Virus Resistance" filed on Dec. 30, 1994, and incorporated by reference herein) were transformed into the *A. tumefaciens* strains C58Z707 (obtained from Dr. A. G. Hepburn, University of Illinois, Urbana, Ill.) and Mog301 (obtained from Mogen NV, Leiden, The Netherlands). The resulting Agrobacteria strains have been used for plant transformations.

C. Cloning, Sequencing, and Engineering PRV Brazil Coat Protein Gene

A virion preparation of PRV Brazil isolate was prepared by Dr. Gonsalves. Subsequently, virion RNA and reverse transcribed signal stranded cDNA were isolated. Coat protein sequences were amplified by PCR; 5S and 3' terminal NcoI sites were installed during the PCR to amplify the coat protein sequence as described by the "proteolytic sites" described in Quemada et al. (1990). Subsequently, the NcoI fragment obtain by PCR amplification was cloned into pGMM (derived from phagemid pBLUESCRIPT II SK (+) [Strategene, La Jolla, CA] to obtain pGMM/PRV-Brcp-7-2.

The CP coding sequence of pGMM/PRV-Brcp-7-2 was nucleotide sequenced with the use of US Biochemical (Cleveland, Ohio) Sequenase Version II sequencing Kit (FIG. 8). The predicted coat protein sequence of the PRV Brazil isolate is shown in FIG. 9. Comparison with the coat protein genes of seven different PRV strains shows that the CP gene of Brazil PRV differed from characterized coat protein sequences of other PRV strains (FIGS. 8, 9, and 10).

After the CP gene was sequenced, NcoI fragments were prepared and inserted into the NcoI site of the expression cassette pUC1318cpexpress. Subsequently, HindIII fragments harboring PRV Brazil coat protein sense cassette were inserted into the HindIII site of the binary plasmid pGA482G. The resulting binary plasmid was transformed into *A. tumefaciens* strains C58Z707 and Mog301. The resulting Agrobacteria strains were used for plant transformations.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule encoding the coat protein of the FLA83 W strain of papaya ringspot virus comprising the nucleotide sequence shown in SEQ ID NO:1 or SEQ ID NO:4.

2. A vector comprising a chimeric expression cassette comprising the DNA molecule of claim 1, a promoter and a polyadenylation signal, wherein the promoter is operably linked to the DNA molecule, and the DNA molecule is operably linked to the polyadenylation signal.

3. The vector of claim 2 wherein the promoter is the cauliflower mosaic virus 35S promoter.

4. The vector of claim 3 wherein the polyadenylation signal is the polyadenylation signal of the cauliflower mosaic virus 35S gene.

5. A bacterial cell comprising the vector of claim 2.

6. The bacterial cell of claim 5 wherein the bacterial cell is selected from the group consisting of an *Agrobacterium tumefaciens* cell and an *Agrobacterium rhizogenes* cell.

7. A transformed plant cell transformed with the vector of claim 2.

8. The transformed plant cell of claim 7, wherein the promoter is the cauliflower mosaic virus 35S promoter and the polyadenylation signal is the polyadenylation signal of the cauliflower mosaic virus 35S gene.

9. A plant selected from the family Cucurbitaceae comprising at least one transformed cell of claim 7.

10. A method of preparing a papaya ringspot viral resistant plant comprising:

(a) transforming plant cells with a chimeric expression cassette comprising a promoter functional in plant cells operably linked to a DNA molecule that encodes a coat protein, wherein the DNA molecule is from the papaya ringspot virus strain FLA83 W and wherein the DNA molecule comprises the nucleotide sequence shown in SEQ ID NO:1 or SEQ ID NO:4.

(b) regenerating the plant cells to provide a differentiated plant; and (c) identifying a transformed plant that comprises the chimeric expression cassette and is resistant to infection by papaya ringspot virus.

11. The method of claim 10 wherein the plant is selected from the family Cucurbitaceae.

12. A vector comprising a chimeric expression cassette comprising the DNA molecule of claim 1 and at least one chimeric expression cassette comprising a DNA molecule selected from the group consisting of a heterologous PRV coat protein gene, a cucumber mosaic virus coat protein gene, a squash mosaic virus coat protein gene, a zucchini yellow mosaic virus coat protein gene, and a watermelon mosaic virus-2 coat protein gene, wherein each expression cassette comprises a promoter and a polyadenylation signal, wherein the promoter is operably linked to the DNA molecule and the DNA molecule is operably linked to the polyadenylation signal.

13. A bacterial cell comprising the vector of claim 12.

14. A transformed plant cell transformed with the vector of claim 12.

15. The transformed plant cell of claim 14 wherein the promoter is the cauliflower mosaic virus 35S promoter and the polyadenylation signal is the polyadenylation signal of the cauliflower mosaic virus 35S gene.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1158 base pairs
      (B) TYPE: nucleic acid
      (C) STRANDEDNESS: Not Relevant
      (D) TOPOLOGY: Not Relevant (ii) MOLECULE TYPE: DNA (genomic)

(ix) FEATURE:
      (A) NAME/KEY: CDS
      (B) LOCATION: 1..1102

(ix) FEATURE:
      (A) NAME/KEY: CDS
      (B) LOCATION: 1105..1158

(xi) SEQUENCE DESCRIPTION: SEQ ID NO:1:

```
ATG GCT CCA TTC AAT GAG CTG GCG AAA CAA GGG AGG GCC CCA TAC GTC         48
Met Ala Pro Phe Asn Glu Leu Ala Lys Gln Gly Arg Ala Pro Tyr Val
 1               5                  10                  15

TCG GAA GTT GGA TTA AGA AGG TTG TAT ACG TGT GAA CGC GGA TCA GTG         96
Ser Glu Val Gly Leu Arg Arg Leu Tyr Thr Cys Glu Arg Gly Ser Val
                20                  25                  30

GAT GAA TTG GAA GCG TAT ATA GAT AAA TAT TTT GAG CGT GAG AGG GGA        144
Asp Glu Leu Glu Ala Tyr Ile Asp Lys Tyr Phe Glu Arg Glu Arg Gly
             35                  40                  45

GAC TCA CCC GAA GTA CTG GTG TAC CAT GAA TCA AGG AGT ACT GAT GAT        192
Asp Ser Pro Glu Val Leu Val Tyr His Glu Ser Arg Ser Thr Asp Asp
 50                  55                  60

TAT GAA CTT GTT CGT GTC AAC AAT ACA CAT GTG TTT CAT CAA GCC AAA        240
Tyr Glu Leu Val Arg Val Asn Asn Thr His Val Phe His Gln Ala Lys
 65                  70                  75                  80

AAT GAA GCT GTG GAC GCT GGT TTG AAC GAA AAG CTC AAA GAA AAA GAA        288
Asn Glu Ala Val Asp Ala Gly Leu Asn Glu Lys Leu Lys Glu Lys Glu
                85                  90                  95

AAA CAG AGA GAG AAA GAA AAA GAA AAA CAA AAA GAG AAA GAA AAA GAT        336
Lys Gln Arg Glu Lys Glu Lys Glu Lys Gln Lys Glu Lys Glu Lys Asp
                100                 105                 110

GAT GCT AGT GAC GGA AAT GAT GTG TTA ACT AGC ACA AAA ACT GGA GAG        384
Asp Ala Ser Asp Gly Asn Asp Val Leu Thr Ser Thr Lys Thr Gly Glu
            115                 120                 125

AGA GAT AGA GAT GTC AAT GTT GGA ACT AGT GGG ACT TTC ACT ATT CCA        432
Arg Asp Arg Asp Val Asn Val Gly Thr Ser Gly Thr Phe Thr Ile Pro
        130                 135                 140

AGG ATT AAA CCA TTC AAT GAT AAG ATG ATT TTA CCG AGA ATT AAG GGA        480
Arg Ile Lys Pro Phe Asn Asp Lys Met Ile Leu Pro Arg Ile Lys Gly
145                 150                 155                 160

AAA ACT GTC CTT AAT TTA AAT CAT CTT CTT CAG TAT AAT CCG CAA CAA        528
Lys Thr Val Leu Asn Leu Asn His Leu Leu Gln Tyr Asn Pro Gln Gln
                165                 170                 175

ATT GAC ATT TCG AAC ACT CGT GCC ACT CAG TCA CAA TTT GAA AAA TGG        576
Ile Asp Ile Ser Asn Thr Arg Ala Thr Gln Ser Gln Phe Glu Lys Trp
                180                 185                 190

CAC GAG GGA GTG AGG AAT GAT TAT GGC CTG AAT GAT AAA GAG ATG GAA        624
His Glu Gly Val Arg Asn Asp Tyr Gly Leu Asn Asp Lys Glu Met Glu
            195                 200                 205
```

```
GTA ATG TTA AAT GGC TTG ATG GTT TGG TGT ATT GAG AAT GGT ACA TCT      672
Val Met Leu Asn Gly Leu Met Val Trp Cys Ile Glu Asn Gly Thr Ser
    210                 215                 220

CCG GAC ATA TCT GGT GTC TGG GTT ATG ATG GAT GAT ACT ACA GGA ACC      720
Pro Asp Ile Ser Gly Val Trp Val Met Met Asp Asp Thr Thr Gly Thr
225                 230                 235                 240

CAA GTT GAT TAT CCA ATC AAG CCT TTA ATT GAG CAT GCT ACT CCG TCA      768
Gln Val Asp Tyr Pro Ile Lys Pro Leu Ile Glu His Ala Thr Pro Ser
                245                 250                 255

TTT AGG CAA ATT ATG GCT CAC TTT AGT AAC GCG GCA GAA GCA TAC ATT      816
Phe Arg Gln Ile Met Ala His Phe Ser Asn Ala Ala Glu Ala Tyr Ile
            260                 265                 270

GCA AGG AGA AAT GCT ACT GAG AGG TAC ATG CCG CGG TAT GGA ATC AAG      864
Ala Arg Arg Asn Ala Thr Glu Arg Tyr Met Pro Arg Tyr Gly Ile Lys
        275                 280                 285

AGA AAT TTG ACT GAC ATT AGC CTC GCT AGA TAC GCT TTC GAT TTC TAT      912
Arg Asn Leu Thr Asp Ile Ser Leu Ala Arg Tyr Ala Phe Asp Phe Tyr
    290                 295                 300

GAG GTT AAT TCG AAA ACA CCT GAT AGG GCT CGC GAA GCT CGC ATG CAG      960
Glu Val Asn Ser Lys Thr Pro Asp Arg Ala Arg Glu Ala Arg Met Gln
305                 310                 315                 320

ATG AAA GCT GCA GCG CTG CGA AAC ACT AAT CGC AGA ATG TTT GGT ATG     1008
Met Lys Ala Ala Ala Leu Arg Asn Thr Asn Arg Arg Met Phe Gly Met
                325                 330                 335

GAC GGC AGT GTC AGT AAC AAG GAA GAA AAT ACG GAG AGA CAC ACA GTG     1056
Asp Gly Ser Val Ser Asn Lys Glu Glu Asn Thr Glu Arg His Thr Val
            340                 345                 350

GAA GAT GTC AAT AGA GAC ATG CAC TCT CTC CTG GGT ATG CGC AAC T       1102
Glu Asp Val Asn Arg Asp Met His Ser Leu Leu Gly Met Arg Asn
        355                 360                 365

GA ATA CTC GCG CTT GTG TGT TTG TCG AGT CTA ACT CGA CCC TGT TTC      1149
   Ile Leu Ala Leu Val Cys Leu Ser Ser Leu Thr Arg Pro Cys Phe
   1               5                  10                  15

ACC CCA TGG                                                         1158
Thr Pro Trp (2) INFORMATION FOR SEQ ID NO:2:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Pro Phe Asn Glu Leu Ala Lys Gln Gly Arg Ala Pro Tyr Val
1               5                   10                  15

Ser Glu Val Gly Leu Arg Arg Leu Tyr Thr Cys Glu Arg Gly Ser Val
                20                  25                  30

Asp Glu Leu Glu Ala Tyr Ile Asp Lys Tyr Phe Glu Arg Glu Arg Gly
            35                  40                  45

Asp Ser Pro Glu Val Leu Val Tyr His Glu Ser Arg Ser Thr Asp Asp
        50                  55                  60

Tyr Glu Leu Val Arg Val Asn Asn Thr His Val Phe His Gln Ala Lys
65                  70                  75                  80

Asn Glu Ala Val Asp Ala Gly Leu Asn Glu Lys Leu Lys Glu Lys Glu
                85                  90                  95

Lys Gln Arg Glu Lys Glu Lys Glu Lys Gln Lys Glu Lys Glu Lys Asp
                100                 105                 110
```

Asp Ala Ser Asp Gly Asn Asp Val Leu Thr Ser Thr Lys Thr Gly Glu
            115                 120                 125

Arg Asp Arg Asp Val Asn Val Gly Thr Ser Gly Thr Phe Thr Ile Pro
        130                 135                 140

Arg Ile Lys Pro Phe Asn Asp Lys Met Ile Leu Pro Arg Ile Lys Gly
145                 150                 155                 160

Lys Thr Val Leu Asn Leu Asn His Leu Leu Gln Tyr Asn Pro Gln Gln
                165                 170                 175

Ile Asp Ile Ser Asn Thr Arg Ala Thr Gln Ser Gln Phe Glu Lys Trp
            180                 185                 190

His Glu Gly Val Arg Asn Asp Tyr Gly Leu Asn Asp Lys Glu Met Glu
        195                 200                 205

Val Met Leu Asn Gly Leu Met Val Trp Cys Ile Glu Asn Gly Thr Ser
    210                 215                 220

Pro Asp Ile Ser Gly Val Trp Val Met Met Asp Asp Thr Thr Gly Thr
225                 230                 235                 240

Gln Val Asp Tyr Pro Ile Lys Pro Leu Ile Glu His Ala Thr Pro Ser
                245                 250                 255

Phe Arg Gln Ile Met Ala His Phe Ser Asn Ala Ala Glu Ala Tyr Ile
            260                 265                 270

Ala Arg Arg Asn Ala Thr Glu Arg Tyr Met Pro Arg Tyr Gly Ile Lys
        275                 280                 285

Arg Asn Leu Thr Asp Ile Ser Leu Ala Arg Tyr Ala Phe Asp Phe Tyr
290                 295                 300

Glu Val Asn Ser Lys Thr Pro Asp Arg Ala Arg Glu Ala Arg Met Gln
305                 310                 315                 320

Met Lys Ala Ala Ala Leu Arg Asn Thr Asn Arg Arg Met Phe Gly Met
                325                 330                 335

Asp Gly Ser Val Ser Asn Lys Glu Glu Asn Thr Glu Arg His Thr Val
            340                 345                 350

Glu Asp Val Asn Arg Asp Met His Ser Leu Leu Gly Met Arg Asn
        355                 360                 365

(2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:3:

Ile Leu Ala Leu Val Cys Leu Ser Ser Leu Thr Arg Pro Cys Phe Thr
1               5                   10                  15

Pro Trp (2) INFORMATION FOR SEQ ID NO:4:

(i) SEQUENCE CHARACTERISTICS:
        (A) LENGTH: 929 base pairs
        (B) TYPE: nucleic acid
        (C) STRANDEDNESS: Not Relevant
        (D) TOPOLOGY: Not Relevant (ii) MOLECULE TYPE: DNA (genomic)

(ix) FEATURE:
        (A) NAME/KEY: CDS
        (B) LOCATION: 3..872

(ix) FEATURE:
    (A) NAME/KEY: CDS
    (B) LOCATION: 876..929

(xi) SEQUENCE DESCRIPTION: SEQ ID NO:4:

```
CC ATG GCC AAG AAT GAA GCT GTG GAC GCT GGT TTG AAC GAA AAG CTC         47
   Met Ala Lys Asn Glu Ala Val Asp Ala Gly Leu Asn Glu Lys Leu
   1               5                  10                  15

AAA GAA AAA GAA AAA CAG AGA GAG AAA GAA AAA GAA AAA CAA AAA GAG        95
Lys Glu Lys Glu Lys Gln Arg Glu Lys Glu Lys Glu Lys Gln Lys Glu
                20                  25                  30

AAA GAA AAA GAT GAT GCT AGT GAC GGA AAT GAT GTG TTA ACT AGC ACA       143
Lys Glu Lys Asp Asp Ala Ser Asp Gly Asn Asp Val Leu Thr Ser Thr
                35                  40                  45

AAA ACT GGA GAG AGA GAT AGA GAT GTC AAT GTT GGA ACT AGT GGG ACT       191
Lys Thr Gly Glu Arg Asp Arg Asp Val Asn Val Gly Thr Ser Gly Thr
    50                  55                  60

TTC ACT ATT CCA AGG ATT AAA CCA TTC AAT GAT AAG ATG ATT TTA CCG       239
Phe Thr Ile Pro Arg Ile Lys Pro Phe Asn Asp Lys Met Ile Leu Pro
65                  70                  75

AGA ATT AAG GGA AAA ACT GTC CTT AAT TTA AAT CAT CTT CTT CAG TAT       287
Arg Ile Lys Gly Lys Thr Val Leu Asn Leu Asn His Leu Leu Gln Tyr
80                  85                  90                  95

AAT CCG CAA CAA ATT GAC ATT TCG AAC ACT CGT GCC ACT CAG TCA CAA       335
Asn Pro Gln Gln Ile Asp Ile Ser Asn Thr Arg Ala Thr Gln Ser Gln
                100                 105                 110

TTT GAA AAA TGG CAC GAG GGA GTG AGG AAT GAT TAT GGC CTG AAT GAT       383
Phe Glu Lys Trp His Glu Gly Val Arg Asn Asp Tyr Gly Leu Asn Asp
            115                 120                 125

AAA GAG ATG GAA GTA ATG TTA AAT GGC TTG ATG GTT TGG TGT ATT GAG       431
Lys Glu Met Glu Val Met Leu Asn Gly Leu Met Val Trp Cys Ile Glu
        130                 135                 140

AAT GGT ACA TCT CCG GAC ATA TCT GGT GTC TGG GTT ATG ATG GAT GAT       479
Asn Gly Thr Ser Pro Asp Ile Ser Gly Val Trp Val Met Met Asp Asp
    145                 150                 155

ACT ACA GGA ACC CAA GTT GAT TAT CCA ATC AAG CCT TTA ATT GAG CAT       527
Thr Thr Gly Thr Gln Val Asp Tyr Pro Ile Lys Pro Leu Ile Glu His
160                 165                 170                 175

GCT ACT CCG TCA TTT AGG CAA ATT ATG GCT CAC TTT AGT AAC GCG GCA       575
Ala Thr Pro Ser Phe Arg Gln Ile Met Ala His Phe Ser Asn Ala Ala
                180                 185                 190

GAA GCA TAC ATT GCA AGG AGA AAT GCT ACT GAG AGG TAC ATG CCG CGG       623
Glu Ala Tyr Ile Ala Arg Arg Asn Ala Thr Glu Arg Tyr Met Pro Arg
            195                 200                 205

TAT GGA ATC AAG AGA AAT TTG ACT GAC ATT AGC CTC GCT AGA TAC GCT       671
Tyr Gly Ile Lys Arg Asn Leu Thr Asp Ile Ser Leu Ala Arg Tyr Ala
        210                 215                 220

TTC GAT TTC TAT GAG GTT AAT TCG AAA ACA CCT GAT AGG GCT CGC GAA       719
Phe Asp Phe Tyr Glu Val Asn Ser Lys Thr Pro Asp Arg Ala Arg Glu
    225                 230                 235

GCT CAC ATG CAG ATG AAA GCT GCA GCG CTG CGA AAC ACT AAT CGC AGA       767
Ala His Met Gln Met Lys Ala Ala Ala Leu Arg Asn Thr Asn Arg Arg
240                 245                 250                 255

ATG TTT GGT ATG GAC GGC AGT GTC AGT AAC AAG GAA GAA AAT ACG GAG       815
Met Phe Gly Met Asp Gly Ser Val Ser Asn Lys Glu Glu Asn Thr Glu
                260                 265                 270

AGA CAC ACA GTG GAA GAT GTC AAT AGA GAC ATG CAC TCT CTC CTG GGT       863
Arg His Thr Val Glu Asp Val Asn Arg Asp Met His Ser Leu Leu Gly
            275                 280                 285

ATG CGC AAC TGA ATA CTC GCG CTT GTG TGT TTG TCG AGT CTA ACT CGA       911
Met Arg Asn     Ile Leu Ala Leu Val Cys Leu Ser Ser Leu Thr Arg
```

```
                 290        1              5                      10
CCC TGT TTC ACC CCA TGG                                                                929
Pro Cys Phe Thr Pro Trp
                 15
```

(2) INFORMATION FOR SEQ ID NO:5:

(i) SEQUENCE CHARACTERISTICS:
        (A) LENGTH: 290 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ala Lys Asn Glu Ala Val Asp Ala Gly Leu Asn Glu Lys Leu Lys
 1               5                  10                  15

Glu Lys Glu Lys Gln Arg Glu Lys Glu Lys Glu Lys Gln Lys Glu Lys
            20                  25                  30

Glu Lys Asp Asp Ala Ser Asp Gly Asn Asp Val Leu Thr Ser Thr Lys
        35                  40                  45

Thr Gly Glu Arg Asp Arg Asp Val Asn Val Gly Thr Ser Gly Thr Phe
 50                  55                  60

Thr Ile Pro Arg Ile Lys Pro Phe Asn Asp Lys Met Ile Leu Pro Arg
 65                  70                  75                  80

Ile Lys Gly Lys Thr Val Leu Asn Leu Asn His Leu Leu Gln Tyr Asn
                85                  90                  95

Pro Gln Gln Ile Asp Ile Ser Asn Thr Arg Ala Thr Gln Ser Gln Phe
            100                 105                 110

Glu Lys Trp His Glu Gly Val Arg Asn Asp Tyr Gly Leu Asn Asp Lys
        115                 120                 125

Glu Met Glu Val Met Leu Asn Gly Leu Met Val Trp Cys Ile Glu Asn
130                 135                 140

Gly Thr Ser Pro Asp Ile Ser Gly Val Trp Val Met Met Asp Asp Thr
145                 150                 155                 160

Thr Gly Thr Gln Val Asp Tyr Pro Ile Lys Pro Leu Ile Glu His Ala
                165                 170                 175

Thr Pro Ser Phe Arg Gln Ile Met Ala His Phe Ser Asn Ala Ala Glu
            180                 185                 190

Ala Tyr Ile Ala Arg Arg Asn Ala Thr Glu Arg Tyr Met Pro Arg Tyr
        195                 200                 205

Gly Ile Lys Arg Asn Leu Thr Asp Ile Ser Leu Ala Arg Tyr Ala Phe
210                 215                 220

Asp Phe Tyr Glu Val Asn Ser Lys Thr Pro Asp Arg Ala Arg Glu Ala
225                 230                 235                 240

His Met Gln Met Lys Ala Ala Ala Leu Arg Asn Thr Asn Arg Arg Met
                245                 250                 255

Phe Gly Met Asp Gly Ser Val Ser Asn Lys Glu Glu Asn Thr Glu Arg
            260                 265                 270

His Thr Val Glu Asp Val Asn Arg Asp Met His Ser Leu Leu Gly Met
        275                 280                 285

Arg Asn
290
```

(2) INFORMATION FOR SEQ ID NO:6:

(i) SEQUENCE CHARACTERISTICS:
        (A) LENGTH: 18 amino acids

```
            (B) TYPE: amino acid
            (D) TOPOLOGY: linear (ii) MOLECULE TYPE: protein (xi) SEQUENCE DESCRIPTION: SEQ ID NO:6:

Ile Leu Ala Leu Val Cys Leu Ser Ser Leu Thr Arg Pro Cys Phe Thr
 1               5                  10                  15

Pro Trp (2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: Not Relevant
            (D) TOPOLOGY: Not Relevant (ii) MOLECULE TYPE: DNA (genomic)

(xi) SEQUENCE DESCRIPTION: SEQ ID NO:7:

CGCAGATTTT ACGAATTCGT TCTTG                                          25

(2) INFORMATION FOR SEQ ID NO:8:

(i) SEQUENCE CHARACTERISTICS:
            (A) LENGTH: 45 base pairs
            (B) TYPE: nucleic acid
            (C) STRANDEDNESS: Not Relevant
            (D) TOPOLOGY: Not Relevant (ii) MOLECULE TYPE: DNA (genomic)

(xi) SEQUENCE DESCRIPTION: SEQ ID NO:8:

GAGCTGGGAC AAAGTGGGGT ACCATGATAT ATTCCTAGGC TTATG                    45

(2) INFORMATION FOR SEQ ID NO:9:

(i) SEQUENCE CHARACTERISTICS:
            (A) LENGTH: 45 base pairs
            (B) TYPE: nucleic acid
            (C) STRANDEDNESS: Not Relevant
            (D) TOPOLOGY: Not Relevant (ii) MOLECULE TYPE: DNA (genomic)

(xi) SEQUENCE DESCRIPTION: SEQ ID NO:9:

AACAATACGC ATGTGTTTCC CATGGCCAAG AATGAAGCTC TGGAC                    45

(2) INFORMATION FOR SEQ ID NO:10:

(i) SEQUENCE CHARACTERISTICS:
            (A) LENGTH: 937 base pairs
            (B) TYPE: nucleic acid
            (C) STRANDEDNESS: Not Relevant
            (D) TOPOLOGY: Not Relevant (ii) MOLECULE TYPE: DNA (genomic)

(x) PUBLICATION INFORMATION:
            (A) AUTHORS: Bateson et al.,
            (C) JOURNAL: Arch. Virol.
            (D) VOLUME: 123
            (F) PAGES: 101-
            (G) DATE: 1992

(xi) SEQUENCE DESCRIPTION: SEQ ID NO:10:

TCCAAAAATG AAGCTGTGGA TGCTGGTTTG AACGAAAAGC TCAAAGAAAA AGAAAAACAG    60

AAAGAAAAAG AAAAAGAAAA ACAAAAAGAG AAAGAGAAAG ACGATGCTAG TGACGGAAAT   120
```

```
GATGTGTCAA CTAGCACAAA AACTGGAGAG AGAGATAGAG ATGTCAATGT TGGGACCAGT      180

GGAACTTTCA CTGTTCCAAG AATCAAATCA TTTACTGACA AGATGATTCT ACCAAGAATT      240

AAGGGAAAGA CTGTCCTTAA TTTAAATCAC CTTCTTCAGT ATAACCCGCA ACAAATTGAC      300

ATTTCTAACA CTCGTGCCAC TCAGTCACAA TTTGAGAAGT GGTATGAGGG AGTGAGGAAT      360

GATTATGGCC TTAATGATAA TGAAATGCAA GTGATGCTAA ATGGCTTGAT GGTTTGGTGT      420

ATCGAGAATG GTACATCTCC AGACATATCT GGTGTCTGGG TTATGATGGA TGGGGAAACC      480

CAAGTTGATT ATCCAATCAA GCCTTTAATT GAGCATGCTA CTCCGACATT TAGGCAAATT      540

ATGGCTCACT TTAGTAATGC GGCAGAAGCA TATATTGCAA AGAGAAATGC TACTGAGAGA      600

TACATGCCGC GGTATGGAAT CAAGAGAAAT TTGACTGACA TTAGCCTCGC CAGATACGCT      660

TTCGATTTCT ATGAGGTGAA TTCGAAAACA CCTGATAGGG CTCGCGAAGC TCACATGCAG      720

ATGAAAGCTG CAGCGCTGCG AAACACTAGT CGCAGAATGT TTGGTATGGA CGGCAGTGTT      780

AGTAACAAGG AAGAAAACAT GGAGAGACAC ACAGTGGAAG ATGTCAATAG AGACATGCAC      840

TCTCTCCTGG GTATGCGCAA CTGAATACTC GCACTTGTGT GTTTGTCGGG CCTGGCTCGA      900

CCTTGTTTCA CCTTATAGTA CTATATAAGC ATTAGAA                              937

(2) INFORMATION FOR SEQ ID NO:11:

(i) SEQUENCE CHARACTERISTICS:
        (A) LENGTH: 1194 base pairs
        (B) TYPE: nucleic acid
        (C) STRANDEDNESS: Not Relevant
        (D) TOPOLOGY: Not Relevant (ii) MOLECULE TYPE: DNA (genomic)

(x) PUBLICATION INFORMATION:
        (A) AUTHORS: Yeh et al.,
        (C) JOURNAL: J. Gen. Virol.
        (D) VOLUME: 73
        (F) PAGES: 2531-
        (G) DATE: 1992

(xi) SEQUENCE DESCRIPTION: SEQ ID NO:11:

GATTTTACCA ATGGGTTCTT GAGCAAGCTC CATTCAATGA GTTGGCGAAA CAAGGAAGGG       60

CCCCATACGT CTCGGAAGTT GGATTAAGAA GATTGTACAC AAGTGAACGT GGATCAATGG      120

ACGAATTAGA AGCGTATATA GATAAATACT TTGAGCGTGA GAGAGGAGAC TCGCCCGAAT      180

TACTAGTGTA CCATGAATCA AGGGGCACTG ATGATTATCA ACTTGTTTGT AGCAACAATA      240

CGCATGTGTT TCATCAGTCC AAGAATGAAG CTGTGGATGC TGGTTTGAAT GAAAAACTCA      300

AAGAGAAGGA AAAACAGAAA GAAAAGAAA AGAAAAACA AAAAGAGAAA GAAAAAGACG       360

GTGCTAGTGA CGGAAATGAT GTGTCAACTA GCACAAAAAC TGGAGAGAGA GATAGAGATG      420

TCAATGTTGG GACCAGTGGA ACTTTCACTG TTCCGAGAAT TAAATCATTT ACTGATAAGA      480

TGGTTCTACC GAGAATTAAG GGGAAGACTG TCCTTAATTT AAATCATCTT CTTCAGTACA      540

ATCCGCAACA AATTGACATT TCTAACACTC GTGCCACTCA TTCACAATTT GAGAAGTGGT      600

ATGAGGGAGT GAGGAATGAT TATGGCCTTA ATGATAATGA AATGCAAGTG ATGCTAAATG      660

GTTTGATGGT TTGGTGTATC GAGAATGGTA CATCTCCAGA CATATCTGGT GTCTGGGTTA      720

TGATGGATGG GGAAACCCAA GTTGATTATC CAATCAAGCC TTTGATTGAG CATGCTACTC      780

CGTCATTTAG GCAAATTATG GCTCACTTTA GTAACGCGGC AGAAGCATAC ATTGCGAAGA      840

GAAATGCTAC TGAGAGGTAC ATGCCGCGGT ATGGAATCAA GAGAAATTTG ACTGACATTA      900

GCCTCGCTAG ATACGCTTTC GACTTCTATG AGGTGAATTC GAAAACACCT GATAGGGCTC      960
```

| | | | | | |
|---|---|---|---|---|---|
| GCGAAGCTCA | CATGCAGATG | AAGGCTGCAG | CGCTGCGAAA | CACCAGTCGC | AGAATGTTTG | 1020
| GTATGGACGG | CAGTGTTAGT | AACAAGGAAG | AAAACACGGA | GAGACACACA | GTGGAAGATG | 1080
| TCAATAGAGA | CATGCACTCT | CTCCTGGGTA | TGCGCAACTA | AATACCTGCG | CTTGTGTGTT | 1140
| TGTTGAGTCT | GACTCGACCC | TGTTTCACCT | TATGGTACTA | TATAAGCATT | AGAA | 1194

(2) INFORMATION FOR SEQ ID NO:12:

(i) SEQUENCE CHARACTERISTICS:
        (A) LENGTH: 1194 base pairs
        (B) TYPE: nucleic acid
        (C) STRANDEDNESS: Not Relevant
        (D) TOPOLOGY: Not Relevant (ii) MOLECULE TYPE: DNA (genomic)

(x) PUBLICATION INFORMATION:
        (A) AUTHORS: Quemada et al.,
        (C) JOURNAL: J. Gen. Virol.
        (D) VOLUME: 71
        (F) PAGES: 203-
        (G) DATE: 1990

(xi) SEQUENCE DESCRIPTION: SEQ ID NO:12:

| | | | | | |
|---|---|---|---|---|---|
| GATTTTACCA | ATGGGTTCTT | GAGCAAGCTC | CATTCAATGA | GTTGGCGAAA | CAAGGAAGGG | 60
| CCCCATACGT | CTCGGAAGTT | GGATTAAGAA | GATTGTACAC | AAGTGAACGT | GGATCAATGG | 120
| ACGAATTAGA | AGCGTATATA | GATAAATACT | TTGAGCGTGA | GAGAGGAGAC | TCGCCCGAAT | 180
| TACTAGTGTA | CCATGAATCA | AGGAGCACTG | ATGATTATCA | ACTTGTTTGT | AGCAACAATA | 240
| CGCATGTGTT | TCATCAGTCC | AAGAATGAAG | CTGTGGATGC | TGGTTTGAAT | GAAAAACTCA | 300
| AAGAGAAGGA | AAATCAGAAA | GAAAAGAAA | AGAAAAACA | AAAAGAGAAA | GAAAAAGACG | 360
| GTGCTAGTGA | CGGAAATGAT | GTGTCAACTA | GCACAAAAAC | TGGAGAGAGA | GATAGAGATG | 420
| TCAATGTTGG | GACCAGTGGA | ACTTTCACTG | TTCCGAGAAT | TAAATCATTT | ACTGATAAGA | 480
| TGGTTCTACC | GAGAATTAAG | GGGAAGACTG | TCCTTAATTT | AAATCATCTT | CTTCAGTACA | 540
| ATCCGCAACA | AATTGACATT | TCTAACACTC | GTGCCACTCA | TTCACAATTT | GAGAAGTGGT | 600
| ATGAGGGAGT | GAGGAATGAT | TATGGCCTTA | ATGATAATGA | AATGCAAGTG | ATGCTAAATG | 660
| GTTTGATGGT | TTGGTGTATC | GAGAATGGTA | CATCTCCAGA | CATATCTGGT | GTCTGGGTTA | 720
| TGATGGATGG | GGAAACCCAA | GTTGATTATC | CAATCAAGCC | TTTGATTGAG | CATGCTACTC | 780
| CGTCATTTAG | GCAAATTATG | GCTCACTTTA | GTAACGCGGC | AGAAGCATAC | ATTGCGAAGA | 840
| GAAATGCTAC | TGAGAGGTAC | ATGCCGCGGT | ATGGAATCAA | GAGAAATTTG | ACTGACATTA | 900
| GCCTCGCTAG | ATACGCTTTC | GACTTCTATG | AGGTGAATTC | GAAAACACCT | GATAGGGCTC | 960
| GCGCAAGCTC | ACATGCAGAT | GAAGGCTGCA | GCGCGCGAAA | CACCAGTCGC | AAAATGTTTG | 1020
| GTATGGACGG | CAGTGTTAGT | AACAAGGAAG | AAAACACGGA | GAGACACACA | GTGGAAGATG | 1080
| TCAATAGAGA | CATGCACTCT | CTCCTGGGTA | TGCGCAACTA | AATACCTGCG | CTTGTGTGTT | 1140
| TGTTGAGTCT | GACTCGACCC | TGTTTCACCT | TATGGTACTA | TATAAGCATT | AGAA | 1194

(2) INFORMATION FOR SEQ ID NO:13:

(i) SEQUENCE CHARACTERISTICS:
        (A) LENGTH: 1194 base pairs
        (B) TYPE: nucleic acid
        (C) STRANDEDNESS: Not Relevant
        (D) TOPOLOGY: Not Relevant (ii) MOLECULE TYPE: DNA (genomic)

(x) PUBLICATION INFORMATION:
  (A) AUTHORS: Quemada et al.,
  (C) JOURNAL: J. Gen. Virol.
  (D) VOLUME: 71
  (F) PAGES: 203-
  (G) DATE: 1990

(xi) SEQUENCE DESCRIPTION: SEQ ID NO:13:

```
GATTTTACCA ATGGGTTCTT GAGCAAGCTC CATTCAATGA GTTGGCGAAA CAAGGAAGGG      60

CCCCATACGT CTCGGAAGTT GGATTAAGAA GATTGTACAC AAGTGAACGT GGATCAATGG     120

ATGAATTAGA AGCGTATATA GATAAATACT TTGAGCGTGA GAGAGGAGAC TCACCCGAAT     180

TACTAGTGTA CCATGAATCA AGGAGCACTG ATGATTATCA ACTTGTTTGC AGTAACAATA     240

CACATGTGTT TCATCAGTCC AAAAATGAAG CTGTGGATAC TGGTTTGAAT GAAAAATTCA     300

AGAAAAGGA AAAACAGAAA GAAAAGAAA AGAAAAACA AAAGAGAAA GAAAAGACG          360

ATGCTAGTGA CGGAAATGAT GTGTCAACTA GCACAAAAAC TGGAGAGAGA GATAGAGATG     420

TCAATGTTGG GACCAGTGGA ACTTTCACTG TTCCGAGAAT TAAATCATTT ACTGATAAGA     480

TGATTCTACC GAGAATTAAG GGAAAGTCTG TCCTTAATTT AAATCACCTA CTTCAGTATA     540

ATCCGCAACA AATTGACATT CTAACACTC GTGCCACTCA GTCACAATTT GAGAAGTGGT     600

ATGAGGGAGT GAGGAATGAT TATGGCCTTA ATGATAATGA AATGCAAGTG ATGCTAAATG     660

GTTTGATGGT TTGGTGTATC GAGAATGGTA CATCTCCAGA CATATCTGGT GTCTGGGTTA     720

TGATGGATGG GGAAACCCAA GTTGATTATC CAATCAAGCC TTTAATTGAG CATGCTACTC     780

CGTCATTTAG GCAAATTATG GCTCACTTTA GTAACGCGGC AGAAGCATAC ATTGCGAAAA     840

GAAATGCTAC TGAGAGGTAC ATGCCGCGGT ATGGAATCAA GAGAAATTTG ACTGACATTA     900

GCCTCGCTAG ATACGCTTTC GACTTCTATG AGGTGAATTC GAAAACACCT GATAGGGCTC     960

GCGAAGCCCA CATGCAGATG AAGGCTGCAG CACTGCGAAA CACTAGTCGC AGAATGTTTG    1020

GTATGGACGG CAGTGTTAGT AACAAGGAAG AAAACACGGA GAGACACACA GTGGAAGACG    1080

TCAATAGAGA CATGCACTCT CTCCTGGGTA TGCGCAACTA AATACTTGCG CTTGTGTGTT    1140

TGTCGAGCTT GACTCGACCC TGTTTCACCT TATAGTACTA TATAAGCATT AGAA          1194
```

(2) INFORMATION FOR SEQ ID NO:14:

(i) SEQUENCE CHARACTERISTICS:
    (A) LENGTH: 439 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:14:

```
Arg Asn Lys Gln Asn Leu Trp Phe Met Ser His Arg Gly Ile Leu Ile
1               5                   10                  15

Asp Asp Ile Tyr Ile Pro Lys Leu Glu Pro Glu Arg Ile Val Ala Ile
                20                  25                  30

Leu Glu Trp Asp Lys Ser Lys Leu Pro Glu His Arg Leu Glu Ala Ile
            35                  40                  45

Thr Ala Ala Met Ile Glu Ser Trp Gly Tyr Gly Asp Leu Thr His Gln
        50                  55                  60

Ile Arg Arg Phe Tyr Gln Trp Val Leu Glu Gln Ala Pro Phe Asn Glu
65                  70                  75                  80

Leu Ala Lys Gln Gly Arg Ala Pro Tyr Val Ser Glu Val Gly Leu Arg
                85                  90                  95
```

-continued

```
Arg Leu Tyr Thr Ser Glu Arg Gly Ser Met Asp Glu Leu Glu Ala Tyr
            100                 105                 110
Ile Asp Lys Tyr Phe Glu Arg Glu Arg Gly Asp Ser Pro Glu Leu Leu
            115                 120                 125
Val Tyr His Glu Ser Arg Gly Thr Asp Asp Tyr Gln Leu Val Cys Ser
130                 135                 140
Asn Asn Thr His Val Phe His Gln Ser Lys Asn Glu Ala Val Asp Ala
145                 150                 155                 160
Gly Leu Asn Glu Lys Leu Lys Glu Lys Glu Gln Lys Glu Lys Glu
            165                 170                 175
Lys Glu Lys Gln Lys Glu Lys Glu Lys Asp Gly Ala Ser Asp Gly Asn
            180                 185                 190
Asp Val Ser Thr Ser Thr Lys Thr Gly Glu Arg Asp Arg Asp Val Asn
            195                 200                 205
Val Gly Thr Ser Gly Thr Phe Thr Val Pro Arg Ile Lys Ser Phe Thr
210                 215                 220
Asp Lys Met Val Leu Pro Arg Ile Lys Gly Lys Thr Val Leu Asn Leu
225                 230                 235                 240
Asn His Leu Leu Gln Tyr Asn Pro Gln Gln Ile Asp Ile Ser Asn Thr
            245                 250                 255
Arg Ala Thr His Ser Gln Phe Glu Lys Trp Tyr Glu Gly Val Arg Asn
            260                 265                 270
Asp Tyr Gly Leu Asn Asp Asn Glu Met Gln Val Met Leu Asn Gly Leu
            275                 280                 285
Met Val Trp Cys Ile Glu Asn Gly Thr Ser Pro Asp Ile Ser Gly Val
            290                 295                 300
Trp Val Met Met Asp Gly Glu Thr Gln Val Asp Tyr Pro Ile Lys Pro
305                 310                 315                 320
Leu Ile Glu His Ala Thr Pro Ser Phe Arg Gln Ile Met Ala His Phe
            325                 330                 335
Ser Asn Ala Ala Glu Ala Tyr Ile Ala Lys Arg Asn Ala Thr Glu Arg
            340                 345                 350
Tyr Met Pro Arg Tyr Gly Ile Lys Arg Asn Leu Thr Asp Ile Ser Leu
            355                 360                 365
Ala Arg Tyr Ala Phe Asp Phe Tyr Glu Val Asn Ser Lys Thr Pro Asp
370                 375                 380
Arg Ala Arg Glu Ala His Met Gln Met Lys Ala Ala Ala Leu Arg Asn
385                 390                 395                 400
Thr Ser Arg Arg Met Phe Gly Met Asp Gly Ser Val Ser Asn Lys Glu
            405                 410                 415
Glu Asn Thr Glu Arg His Thr Val Glu Asp Val Asn Arg Asp Met His
            420                 425                 430
Ser Leu Leu Gly Met Arg Asn
            435
```

(2) INFORMATION FOR SEQ ID NO:15:

(i) SEQUENCE CHARACTERISTICS:
      (A) LENGTH: 379 amino acids
      (B) TYPE: amino acid
      (C) STRANDEDNESS: Not Relevant
      (D) TOPOLOGY: Not Relevant (ii) MOLECULE TYPE: protein (xi) SEQUENCE DESCRIPTION: SEQ ID NO:15:

Leu Thr His Gln Ile Arg Arg Phe Tyr Gln Trp Val Leu Glu Gln Ala

```
 1               5                  10                 15
Pro Phe Asn Glu Leu Ala Lys Gln Gly Arg Ala Pro Tyr Val Ser Glu
                20                  25                 30

Val Gly Leu Arg Arg Leu Tyr Thr Ser Glu Arg Gly Ser Met Asp Glu
                35                  40                 45

Leu Glu Ala Tyr Ile Asp Lys Tyr Phe Glu Arg Glu Arg Gly Asp Ser
                50                  55                 60

Pro Glu Leu Leu Val Tyr His Glu Ser Arg Ser Thr Asp Asp Tyr Gln
 65                 70                  75                 80

Leu Val Cys Ser Asn Asn Thr His Val Phe His Gln Ser Lys Asn Glu
                85                  90                 95

Ala Val Asp Ala Gly Leu Asn Glu Lys Leu Lys Glu Lys Glu Asn Gln
               100                 105                110

Lys Glu Lys Glu Lys Glu Lys Gln Lys Glu Lys Glu Lys Asp Gly Ala
               115                 120                125

Ser Asp Gly Asn Asp Val Ser Thr Ser Thr Lys Thr Gly Glu Arg Asp
               130                 135                140

Arg Asp Val Asn Val Gly Thr Ser Gly Thr Phe Thr Val Pro Arg Ile
145                150                 155                160

Lys Ser Phe Thr Asp Lys Met Val Leu Pro Arg Ile Lys Gly Lys Thr
               165                 170                175

Val Leu Asn Leu Asn His Leu Leu Gln Tyr Asn Pro Gln Gln Ile Asp
               180                 185                190

Ile Ser Asn Thr Arg Ala Thr His Ser Gln Phe Glu Lys Trp Tyr Glu
               195                 200                205

Gly Val Arg Asn Asp Tyr Gly Leu Asn Asp Asn Glu Met Gln Val Met
               210                 215                220

Leu Asn Gly Leu Met Val Trp Cys Ile Glu Asn Gly Thr Ser Pro Asp
225                230                 235                240

Ile Ser Gly Val Trp Val Met Met Asp Gly Glu Thr Gln Val Asp Tyr
               245                 250                255

Pro Ile Lys Pro Leu Ile Glu His Ala Thr Pro Ser Phe Arg Gln Ile
               260                 265                270

Met Ala His Phe Ser Asn Ala Ala Glu Ala Tyr Ile Ala Lys Arg Asn
               275                 280                285

Ala Thr Glu Arg Tyr Met Pro Arg Tyr Gly Ile Lys Arg Asn Leu Thr
               290                 295                300

Asp Ile Ser Leu Ala Arg Tyr Ala Phe Asp Phe Tyr Glu Val Asn Ser
305                310                 315                320

Lys Thr Pro Asp Arg Ala Arg Glu Ala His Met Gln Met Lys Ala Ala
               325                 330                335

Ala Leu Arg Asn Thr Ser Arg Lys Met Phe Gly Met Asp Gly Ser Val
               340                 345                350

Ser Asn Lys Glu Glu Asn Thr Glu Arg His Thr Val Glu Asp Val Asn
               355                 360                365

Arg Asp Met His Ser Leu Leu Gly Met Arg Asn
370                375
```

(2) INFORMATION FOR SEQ ID NO:16:

(i) SEQUENCE CHARACTERISTICS:
        (A) LENGTH: 392 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:16:

```
Ile Thr Ala Ala Met Ile Glu Ser Trp Gly Tyr Gly Asp Leu Thr His
  1               5                  10                  15

Gln Ile Arg Arg Phe Tyr Gln Trp Val Leu Glu Gln Ala Pro Phe Asn
             20                  25                  30

Glu Leu Ala Lys Gln Gly Arg Ala Pro Tyr Val Ser Glu Val Gly Leu
         35                  40                  45

Arg Arg Leu Tyr Thr Ser Glu Arg Gly Ser Met Asp Glu Leu Glu Ala
 50                  55                  60

Tyr Ile Asp Lys Tyr Phe Glu Arg Glu Arg Gly Asp Ser Pro Glu Leu
 65                  70                  75                  80

Leu Val Tyr His Glu Ser Arg Ser Thr Asp Asp Tyr Gln Leu Val Cys
                 85                  90                  95

Ser Asn Asn Thr His Val Phe His Gln Ser Lys Asn Glu Ala Val Asp
            100                 105                 110

Thr Gly Leu Asn Glu Lys Phe Lys Glu Lys Glu Lys Gln Lys Glu Lys
        115                 120                 125

Glu Lys Glu Lys Gln Lys Glu Lys Asp Asp Ala Ser Asp Gly
130                 135                 140

Asn Asp Val Ser Thr Ser Thr Lys Thr Gly Glu Arg Asp Arg Asp Val
145                 150                 155                 160

Asn Val Gly Thr Ser Gly Thr Phe Thr Val Pro Arg Ile Lys Ser Phe
                165                 170                 175

Thr Asp Lys Met Ile Leu Pro Arg Ile Lys Gly Lys Ser Val Leu Asn
            180                 185                 190

Leu Asn His Leu Leu Gln Tyr Asn Pro Gln Gln Ile Asp Ile Ser Asn
        195                 200                 205

Thr Arg Ala Thr Gln Ser Gln Phe Glu Lys Trp Tyr Glu Gly Val Arg
210                 215                 220

Asn Asp Tyr Gly Leu Asn Asp Asn Glu Met Gln Val Met Leu Asn Gly
225                 230                 235                 240

Leu Met Val Trp Cys Ile Glu Asn Gly Thr Ser Pro Asp Ile Ser Gly
                245                 250                 255

Val Trp Val Met Met Asp Gly Glu Thr Gln Val Asp Tyr Pro Ile Lys
            260                 265                 270

Pro Leu Ile Glu His Ala Thr Pro Ser Phe Arg Gln Ile Met Ala His
        275                 280                 285

Phe Ser Asn Ala Ala Glu Ala Tyr Ile Ala Lys Arg Asn Ala Thr Glu
290                 295                 300

Arg Tyr Met Pro Arg Tyr Gly Ile Lys Arg Asn Leu Thr Asp Ile Ser
305                 310                 315                 320

Leu Ala Arg Tyr Ala Phe Asp Phe Tyr Glu Val Asn Ser Lys Thr Pro
                325                 330                 335

Asp Arg Ala Arg Glu Ala His Met Gln Met Lys Ala Ala Ala Leu Arg
            340                 345                 350

Asn Thr Ser Arg Arg Met Phe Gly Met Asp Gly Ser Val Ser Asn Lys
        355                 360                 365

Glu Glu Asn Thr Glu Arg His Thr Val Glu Asp Val Asn Arg Asp Met
370                 375                 380

His Ser Leu Leu Gly Met Arg Asn
385                 390
```

(2) INFORMATION FOR SEQ ID NO:17:

(i) SEQUENCE CHARACTERISTICS:
        (A) LENGTH: 291 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:17:

```
Val Phe His Gln Ser Lys Asn Glu Ala Val Asp Ala Gly Leu Asn Glu
 1               5                  10                  15

Lys Leu Lys Glu Lys Glu Lys Gln Glu Lys Glu Lys Glu Lys Glu Gln
            20                  25                  30

Lys Glu Lys Glu Lys Asp Asp Ala Ser Asp Gly Asn Asp Val Ser Thr
        35                  40                  45

Ser Thr Lys Thr Gly Glu Arg Asp Arg Asp Val Asn Val Gly Thr Ser
    50                  55                  60

Gly Thr Phe Thr Val Pro Arg Ile Lys Ser Phe Thr Asp Lys Met Ile
65                  70                  75                  80

Leu Pro Arg Ile Lys Gly Lys Thr Val Leu Asn Leu Asn His Leu Leu
                85                  90                  95

Gln Tyr Asn Pro Gln Gln Ile Asp Ile Ser Asn Thr Arg Ala Thr Gln
            100                 105                 110

Ser Gln Phe Glu Lys Trp Tyr Glu Gly Val Arg Asn Asp Tyr Gly Leu
        115                 120                 125

Asn Asp Asn Glu Met Gln Val Met Leu Asn Gly Leu Met Val Trp Cys
    130                 135                 140

Ile Glu Asn Gly Thr Ser Pro Asp Ile Ser Gly Val Trp Val Met Met
145                 150                 155                 160

Asp Gly Glu Thr Gln Val Asp Tyr Pro Ile Lys Pro Leu Ile Glu His
                165                 170                 175

Ala Thr Pro Thr Phe Arg Gln Ile Met Ala His Phe Ser Asn Ala Ala
            180                 185                 190

Glu Ala Tyr Ile Ala Lys Arg Asn Ala Thr Glu Arg Tyr Met Pro Arg
        195                 200                 205

Tyr Gly Ile Lys Arg Asn Leu Thr Asp Ile Ser Leu Ala Arg Tyr Ala
    210                 215                 220

Phe Asp Phe Tyr Glu Val Asn Ser Lys Thr Pro Asp Arg Ala Arg Glu
225                 230                 235                 240

Ala His Met Gln Met Lys Ala Ala Leu Arg Asn Thr Ser Arg Arg
                245                 250                 255

Met Phe Gly Met Asp Gly Ser Val Ser Asn Lys Glu Glu Asn Met Glu
            260                 265                 270

Arg His Thr Val Glu Asp Val Asn Arg Asp Met His Ser Leu Leu Gly
        275                 280                 285

Met Arg Asn
    290
```

(2) INFORMATION FOR SEQ ID NO:18:

(i) SEQUENCE CHARACTERISTICS:
        (A) LENGTH: 906 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:18:

| | | | | | |
|---|---|---|---|---|---|
| CCATGGCTGT | GGATGCTGGT | TTGAATGAAA | AGCGTAAAGA | ACAAGAGAAA | CAAGAAGAAA | 60 |
| AAGAAGAAAA | ACAAAAAAAG | AAAGAAAAAG | ACGATGCTAG | TTACGAAAAC | GATGTGTCAA | 120 |
| CTAGCACAAG | AACTGGAGAG | AGAGACAGAG | ATGTCAATGT | TGGGACCAGT | GGAACTTTCA | 180 |
| CTGTTCCGAG | AACAAAATCA | TTTACTGATA | AGATGATTTT | ACCTAGAATT | AAGGGAAAAA | 240 |
| CTGTCCTTAA | TTTAAATCAT | CTGATTCAGT | ATAATCCGCA | ACAAATTGAC | ATTTCTAACA | 300 |
| CTCGTGCTAC | TCAATCACAA | TTTGAGAAGT | GGTACGAGGG | AGTGAGGAAT | GATTATGGCC | 360 |
| TTAATGATAA | TGAGATGCAA | ATAGTGCTAA | ATGGTTTGAT | GGTTTGGTGT | ATCGAAAACG | 420 |
| GTACATCTCC | AGACATATCT | GGTGTCTGGG | TTATGATGGA | TGGGGAAACC | CAGGTTGACT | 480 |
| ATCCAATCAA | GCCTTTAATT | GAGCATGCTA | CTCCGTCGTT | TAGGCAAATT | ATGGCTCATT | 540 |
| TCAGTAACGC | GGCAGAAGCA | TACATTCAA | AGAGAAATGC | TACTGAGAGG | TACATGCCGC | 600 |
| GGTATGGGAT | CAAGAGAAAT | TTGACTGACA | TTAGTCTTGC | TAGATATGCT | TTCGATTTCT | 660 |
| ATGAGGTGAA | TTCGAAAACA | CCTGATAGGG | CTCGCGAAGC | TCACATGCAG | ATGAAAGCTG | 720 |
| CAGCGCTGCG | AAACACTAAT | CGCAGAATGT | TTGGTATGGA | CGGCAGTGTT | AGTAACAAGG | 780 |
| AAGAAAACAC | GGAGAGACAC | ACAGTGGAAG | ATGTCAATAG | AGACATGCAC | TCTCTCCTGG | 840 |
| GTATGCGCAA | CTGAATACTC | GCGCTGGTGC | TTGTTGGGCC | TGACTCGACC | CTGTTTCACC | 900 |
| CCATGG | | | | | | 906 |

(2) INFORMATION FOR SEQ ID NO:19:

(i) SEQUENCE CHARACTERISTICS:
        (A) LENGTH: 1155 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:19:

| | | | | | |
|---|---|---|---|---|---|
| AGCAGGCTCC | ATTCAATGAA | TTAGCGAAGC | AGGGCAGGGC | TCCATATGTG | TCTGAGGTTG | 60 |
| GATTGAGGCG | CTTATACACT | AGTAAGCGTG | GGTCAATGGA | TGAATTGGAG | GCCTACATAG | 120 |
| ATAAATATTT | TGAACGAGAG | AGAGGAGACT | CACCCGAATT | ACTAGTGTAC | CATGAATCGA | 180 |
| GAAGCACTGA | CAATCATCAA | TTAACCCGCG | GCAGTAATAC | ACATGTGTTT | CACCAGTCTA | 240 |
| AAAATGAAGC | TGTGGATACC | GGTCTGAATG | AGAAGCTCAA | AGAAAAGAA | AAGCAGAAAG | 300 |
| AAAAAGAAAA | AGATAAACAA | CAAGATAAAG | ACAATGATGG | AGCTAGTGAC | GGAAACGATG | 360 |
| TGTCAACTAG | CACAAAAACT | GGAGAGAGAG | ATAGGGATGG | CAATGCCGGA | ACTAGTGGAA | 420 |
| CCTTCACTGT | TCCGAGGATA | AAGTCATTTA | CTGATAAGAT | GATCTTACCA | AGAATTAAGG | 480 |
| GAAAAACTGT | CCTTAATTTA | AATCATCTTC | TTCAGTATAA | TCCGAAACAA | GTTGACATCT | 540 |
| CAAACACTCG | CGCCACTCAA | TCTCAATTTG | AGAAGTGGTA | TGAGGGAGTG | AGAAATGATT | 600 |
| ATGGCCTTAA | TGATAACGAA | ATGCAAGTAA | TGTTAAATGG | TTTGATGGTT | TGGTGTATCG | 660 |
| AAAATGGTAC | ATCTCCAGAT | ATATCTGGTG | TCTGGGTTAT | GATGGATGGG | GAAACCCAAG | 720 |
| TCGATTATCC | CATTAAACCT | TTGATTGAAC | ACGCAACTCC | TTCATTTAGG | CAAATCAATG | 780 |
| GCTCACTTCA | GTAACGCGGC | AGAGGCATAC | ATCGCGAAGA | GGAATGCAAC | TGAGAAGTAC | 840 |
| ATGCCGCGGT | ATGGAATCAA | GAGAAATTTG | ACTGACATTA | GTCTCGCTAG | ATATGCTTTC | 900 |
| GATTTCTATG | AGGTGAATTC | GAAAACACCT | GATAGGGCTC | GTGAAGCTCA | TATGCAGATG | 960 |
| AAGGCTGCAG | CGCTACGCAA | TACTAATCGC | AAAATGTTTG | GAATGGACGG | CAGTGTCAGT | 1020 |

```
AACAAGGAAG AAAACACGGA GAGACACACA GTGGAAGATG TCAACAGAGA CATGCACTCT    1080

CTCCTGGGTA TGCGCAATTG AATACTCGCG CTAGTGTGTT TGTCGGGCCT GGCTCGACCC    1140

TGTTTCACCT TATAA                                                      1155
```

(2) INFORMATION FOR SEQ ID NO:20:

(i) SEQUENCE CHARACTERISTICS:
        (A) LENGTH: 366 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:20:

```
Glu Gln Ala Pro Phe Asn Glu Leu Ala Lys Gln Gly Arg Ala Pro Tyr
  1               5                  10                  15

Val Ser Glu Val Gly Leu Arg Arg Leu Tyr Thr Ser Lys Arg Gly Ser
                 20                  25                  30

Met Asp Glu Leu Glu Ala Tyr Ile Asp Lys Tyr Phe Glu Arg Glu Arg
             35                  40                  45

Gly Asp Ser Pro Glu Leu Leu Val Tyr His Glu Ser Arg Ser Thr Asp
 50                  55                  60

Asn His Gln Leu Thr Arg Gly Ser Asn Thr His Val Phe His Gln Ser
 65                  70                  75                  80

Lys Asn Glu Ala Val Asp Thr Gly Leu Asn Glu Lys Leu Lys Glu Lys
                 85                  90                  95

Glu Lys Gln Lys Glu Lys Glu Lys Asp Lys Gln Gln Asp Lys Asp Asn
            100                 105                 110

Asp Gly Ala Ser Asp Gly Asn Asp Val Ser Thr Ser Thr Lys Thr Gly
            115                 120                 125

Glu Arg Asp Arg Asp Val Asn Ala Gly Thr Ser Gly Thr Phe Thr Val
130                 135                 140

Pro Arg Ile Lys Ser Phe Thr Asp Lys Met Ile Leu Pro Arg Ile Lys
145                 150                 155                 160

Gly Lys Thr Val Leu Asn Leu Asn His Leu Leu Gln Tyr Asn Pro Lys
                165                 170                 175

Gln Val Asp Ile Ser Asn Thr Arg Ala Thr Gln Ser Gln Phe Glu Lys
            180                 185                 190

Trp Tyr Glu Gly Val Arg Asn Asp Tyr Gly Leu Asn Asp Asn Glu Met
            195                 200                 205

Gln Val Met Leu Asn Gly Leu Met Val Trp Cys Ile Glu Asn Gly Thr
210                 215                 220

Ser Pro Asp Ile Ser Gly Val Trp Val Met Met Asp Gly Glu Thr Gln
225                 230                 235                 240

Val Asp Tyr Pro Ile Lys Pro Leu Ile Glu His Ala Thr Pro Ser Phe
                245                 250                 255

Arg Gln Ile Met Ala His Phe Ser Asn Ala Ala Glu Ala Tyr Ile Ala
            260                 265                 270

Lys Arg Asn Ala Thr Glu Lys Tyr Met Pro Arg Tyr Gly Ile Lys Arg
            275                 280                 285

Asn Leu Thr Asp Ile Ser Leu Ala Arg Tyr Ala Phe Asp Phe Tyr Glu
290                 295                 300

Val Asn Ser Lys Thr Pro Asp Arg Ala Arg Glu Ala His Met Gln Met
305                 310                 315                 320
```

```
Lys Ala Ala Ala Leu Arg Asn Thr Asn Arg Lys Met Phe Gly Met Asp
            325                 330                 335

Gly Ser Val Ser Asn Lys Glu Glu Asn Thr Glu Arg His Thr Val Glu
            340                 345                 350

Asp Val Asn Arg Asp Met His Ser Leu Leu Gly Met Arg Asn
            355                 360             365
```

(2) INFORMATION FOR SEQ ID NO:21:

(i) SEQUENCE CHARACTERISTICS:
        (A) LENGTH: 283 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:21:

```
Met Ala Val Asp Ala Gly Leu Asn Glu Lys Arg Lys Glu Gln Glu Lys
1               5                   10                  15

Gln Glu Glu Lys Glu Glu Lys Gln Lys Lys Glu Lys Asp Asp Ala
            20                  25                  30

Ser Tyr Gly Asn Asp Val Ser Thr Ser Thr Arg Thr Gly Glu Arg Asp
        35                  40                  45

Arg Asp Val Asn Val Gly Thr Ser Gly Thr Phe Thr Val Pro Arg Thr
    50                  55                  60

Lys Ser Phe Thr Asp Lys Met Ile Leu Pro Arg Ile Lys Gly Lys Thr
65                  70                  75                  80

Val Leu Asn Leu Asn His Leu Ile Gln Tyr Asn Pro Gln Gln Ile Asp
            85                  90                  95

Ile Ser Asn Thr Arg Ala Thr Gln Ser Gln Phe Glu Lys Trp Tyr Glu
            100                 105                 110

Gly Val Arg Asn Asp Tyr Gly Leu Asn Asp Asn Glu Met Gln Ile Val
        115                 120                 125

Leu Asn Gly Leu Met Val Trp Cys Ile Glu Asn Gly Thr Ser Pro Asp
    130                 135                 140

Ile Ser Gly Val Trp Val Met Met Asp Gly Glu Thr Gln Val Asp Tyr
145                 150                 155                 160

Pro Ile Lys Pro Leu Ile Glu His Ala Thr Pro Ser Phe Arg Gln Ile
            165                 170                 175

Met Ala His Phe Ser Asn Ala Ala Glu Ala Tyr Ile Thr Lys Arg Asn
            180                 185                 190

Ala Thr Glu Arg Tyr Met Pro Arg Tyr Gly Ile Lys Arg Asn Leu Thr
        195                 200                 205

Asp Ile Ser Leu Ala Arg Tyr Ala Phe Asp Phe Tyr Glu Val Asn Ser
    210                 215                 220

Lys Thr Pro Asp Arg Ala Arg Glu Ala His Met Gln Met Lys Ala Ala
225                 230                 235                 240

Ala Leu Arg Asn Thr Asn Arg Arg Met Phe Gly Met Asp Gly Ser Val
            245                 250                 255

Ser Asn Lys Glu Glu Asn Thr Glu Arg His Thr Val Glu Asp Val Asn
            260                 265                 270

Arg Asp Met His Ser Leu Leu Gly Met Arg Asn
            275                 280
```